(12) United States Patent
Okano et al.

(10) Patent No.: US 11,135,413 B2
(45) Date of Patent: Oct. 5, 2021

(54) METHOD OF PRODUCING TRANSDERMAL ABSORPTION SHEET

(71) Applicant: FUJIFILM Corporation, Tokyo (JP)

(72) Inventors: Keio Okano, Ashigarakami-gun (JP); Satoshi Wakamatsu, Ashigarakami-gun (JP); Yoshinobu Katagiri, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 481 days.

(21) Appl. No.: 15/695,720

(22) Filed: Sep. 5, 2017

(65) Prior Publication Data
US 2017/0361082 A1  Dec. 21, 2017

Related U.S. Application Data

(63) Continuation of application No. PCT/JP2016/057197, filed on Mar. 8, 2016.

(30) Foreign Application Priority Data

Mar. 10, 2015 (JP) .............. JP2015-047622
Mar. 3, 2016 (JP) .............. JP2016-040831

(51) Int. Cl.
  *B29C 39/02* (2006.01)
  *A61M 37/00* (2006.01)
  *A61K 9/00* (2006.01)

(52) U.S. Cl.
CPC ....... *A61M 37/0015* (2013.01); *A61K 9/0021* (2013.01); *B29C 39/025* (2013.01);
(Continued)

(58) Field of Classification Search
CPC ... B29C 39/021; B29C 39/025; B29C 39/123; B39C 39/40
See application file for complete search history.

(56) References Cited

U.S. PATENT DOCUMENTS

2003/0146692 A1* 8/2003 Uchida ............... H01L 51/0005
                                                        313/504
2012/0027810 A1* 2/2012 Chen ................. A61M 37/0015
                                                        424/400
(Continued)

FOREIGN PATENT DOCUMENTS

CN  101829394 A  9/2010
CN  102553064 A  7/2012
(Continued)

OTHER PUBLICATIONS

Lee, J.W., J.-H. Park, M.R. Prausnitz, Dissolving microneedles for transdermal drug delivery, Biomaterials, vol. 29 (2008), pp. 2113-2124 (Year: 2008).*
(Continued)

*Primary Examiner* — Matthew J Daniels
(74) *Attorney, Agent, or Firm* — Birch, Stewart, Kolasch & Birch, LLP

(57) ABSTRACT

A method of producing a transdermal absorption sheet includes: filling needle-like recessed portions of a mold with a drug solution that is a polymer solution containing a drug; drying the drug solution filling the needle-like recessed portions to form a drug layer containing the drug; supplying a polymer layer forming solution to the mold, the mold provided with a step portion that has a height different from a height of a region in which the needle-like recessed portion is formed in a periphery of the region in which the needle-like recessed portion is formed in a range of equal to or greater than the step portion as seen from above, and then fixing a contact position of the polymer layer forming solution and the mold to the step portion while reducing the polymer layer forming solution; and drying the polymer layer forming solution to form a polymer layer.

13 Claims, 28 Drawing Sheets

(52) U.S. Cl.
CPC ............. *A61M 2037/0023* (2013.01); *A61M 2037/0046* (2013.01); *A61M 2037/0053* (2013.01)

(56) References Cited

U.S. PATENT DOCUMENTS

| | | |
|---|---|---|
| 2012/0078189 A1 | 3/2012 | Ogawa et al. |
| 2015/0238413 A1 | 8/2015 | Mochizuki et al. |

FOREIGN PATENT DOCUMENTS

| | | | | |
|---|---|---|---|---|
| CN | 104056346 A | 9/2014 | | |
| EP | 3266494 A1 | 1/2018 | | |
| JP | 2009-82207 A | 4/2009 | | |
| JP | 2010-213845 A | 9/2010 | | |
| JP | 2011-224332 A | 11/2011 | | |
| JP | 2012-55343 | * | 3/2012 | ........ A61M 37/0015 |
| JP | 2012-196426 A | 10/2012 | | |
| JP | 2013-153866 A | 8/2013 | | |
| JP | 2014-4077 A | 1/2014 | | |
| JP | 2014-23698 A | 2/2014 | | |
| JP | 5770055 B2 | 8/2015 | | |
| WO | WO 2011/095386 A2 | 8/2011 | | |
| WO | WO 2014/077242 A1 | 5/2014 | | |

OTHER PUBLICATIONS

Japanese Notification of Reasons for Refusal for counterpart Japanese Application No. 2016-040831, dated May 8, 2018, with Machine translation.
Extended European Search Report for counterpart Application No. 16761760.4, dated Feb. 28, 2018.
Chinese Office Action Search Report dated Nov. 4, 2019, for counterpart Chinese Patent Application No. 201680013235.1, with English translation.
Korean Grant of Patent dated Oct. 24, 2019, for counterpart Korean Patent Application No. 10-2017-7025161, with English machine translation.
Korean Office Action for counterpart Korean Application No. 10-2017-7025161, dated Apr. 9, 2019, with English translation.
International Preliminary Report on Patentability and Written Opinion of the International Searching Authority (Form PCT/IPEA/409) for International Application No. PCT/JP2016/057197, dated Sep. 9, 2016, including an English translation.
International Search Report and Written Opinion of the International Searching Authority (Forms PCT/ISA/210 and PCT/ISA/237) for International Application No. PCT/JP2016/057197, dated May 17, 2016, including an English translation of the International Search Report.
Japanese Office Action for Japanese Application No. 2016-040831, dated Sep. 20, 2017, including an English translation.
Chinese Office Action dated May 12, 2020, for counterpart Chinese Patent Application No. 201680013235.1, with English translation.

* cited by examiner

METHOD OF PRODUCING TRANSDERMAL ABSORPTION SHEET

CROSS-REFERENCE TO RELATED APPLICATIONS

This application is a Continuation of PCT International Application No. PCT/JP2016/057197 filed on Mar. 8, 2016, which claims priorities under 35 U.S.C. § 119(a) to Japanese Patent Application No. 2015-047622 filed on Mar. 10, 2015 and Japanese Patent Application No. 2016-040831 filed on Mar. 3, 2016. Each of the above applications is hereby expressly incorporated by reference, in their entirety, into the present application.

BACKGROUND OF THE INVENTION

1. Field of the Invention

The present invention relates to a method of producing a transdermal absorption sheet and particularly relates to a method of producing a transdermal absorption sheet in which needle-like protruding portions containing a drug are arranged on a sheet portion thereof.

2. Description of the Related Art

As a method for administering a drug or the like through a living body surface, that is, a skin, a mucous membrane, or the like, a drug injection method of using a transdermal absorption sheet on which needle-like protruding portions having a high aspect ratio and containing a drug (hereinafter, also referred to as "microneedles") are formed and inserting the microneedles into a skin is used. In order to use a sheet as a transdermal absorption sheet, a drug needs to be mixed into the sheet. However, many drugs are expensive, and thus, the drug needs to be contained in the sheet so as to concentrate at the microneedles.

As a method of producing a transdermal absorption sheet, a method is known in which a polymer solution or the like is poured into a mold on which needle-like recessed portions that are inverted shapes of needle-like protruding portions are formed, to transfer the shapes. For example, there is a method including using a mold for microneedle sheets in which through-holes passing through a base material are made at the bottoms of recessed portions, first, coating a surface of the mold with a solution of a diluted drug, subsequently scraping off extra solution using a squeegee or the like, drying the drug solution, and then coating the dried drug solution with a needle raw material.

In addition, there is a method of producing a sheet in which microneedle-like protrusion preparation are accumulated in which the sheet is highly accurately produced in one step by filling a flexible substrate with a thick liquid consisting of a mixture of a target substance and a base utilizing a centrifugal force, while drying and hardening the liquid.

In the formation of the microneedles using shape inversion by a needle-like recessed plate, regardless of whether a drug solution is contained or not, it is necessary to apply a polymer solution to the needle-like recessed plate by a certain method. For example, JP2009-082207A discloses a method of producing a functional film including applying a solution of a polymer resin to a form in which a recessed portion array is formed, and applying pressure with a pressurized fluid to fill the recessed portion array with the solution of the polymer resin. JP2011-224332A discloses use of a pressurizing filling apparatus for filling needle-like recessed portions with a polymer solution. In addition, JP2014-023698A discloses a method including supplying a needle-like body forming solution in a state in which a recessed plate is inclined, and moving the needle-like body forming solution from an upper side to a lower side to fill the recessed portions with the needle-like body forming solution.

SUMMARY OF THE INVENTION

In order to improve the releasability of formed needle-like protruding portions, a needle-like recessed plate is formed by using a material having a low surface tension or is subjected to a surface treatment in some cases. Therefore, in the case of directly applying a polymer solution to the needle-like recessed plate, the liquid is reduced due to a difference in surface tension between a solid and a liquid, and poor wettability, and the liquid is repelled. Thus, there is a problem in that a film cannot be formed.

In order to prevent the liquid from being repelled, it is considered that the surface tension of the needle-like recessed plate portion is increased to decrease the surface tension of the polymer solution. However, from the viewpoint of releasability, it is difficult to increase the surface tension of the needle-like recessed plate portion. In addition, the addition of a surfactant into the polymer solution may be not desirable from the viewpoint of performance. Further, as another viewpoint, an increase in the coating film thickness of the polymer solution can be considered but it is not preferable to apply a load to a drying step or to form an unnecessary sheet in terms of performance from the viewpoint of production costs.

In the methods described in JP2009-082207A, JP2011-224332A, and JP2014-023698A, it is possible to maintain the shape of the frame by suppressing the surface tension. However, a large scale apparatus that includes the entire apparatus is required and thus facility costs increase. In addition, coating and drying cannot be performed more accurately in a static state.

The present invention has been made in consideration of such circumstances, and an object thereof is to provide a method of producing a transdermal absorption sheet capable of performing drying in a state in which each solid form of a polymer solution is stably maintained while suppressing an increase in facility costs by controlling a method of supplying the polymer solution into a frame that partitions the polymer solution.

In order to achieve the above object, the present invention provides a method of producing a transdermal absorption sheet, comprising: a drug solution filling step of filling needle-like recessed portions of a mold having the needle-like recessed portions with a drug solution that is a polymer solution containing a drug; a drug solution drying step of drying the drug solution filling the needle-like recessed portions to form a drug layer containing the drug; a polymer layer forming solution supply step of supplying a polymer layer forming solution to the mold, the mold being provided with a step portion that is higher than a region in which the needle-like recessed portions are formed in a periphery of the region in which the needle-like recessed portions are formed, at a height equal to or higher than a height of the step portion in a range of equal to or greater than the step portion as seen from above; and a polymer layer forming solution drying step of drying the polymer layer forming solution supplied to the mold to form a polymer layer.

According to the present invention, since the step portion that is higher than the region in which the needle-like recessed portions are formed is provided in the periphery of the region in which the needle-like recessed portions are formed on the mold on which the needle-like recessed portions are formed, and the polymer layer forming solution for forming a polymer layer is supplied at a height equal to or higher than the height of the step portion in a range of equal to or greater than the step portion, the polymer layer forming solution can be prevented from being repelled in the region in which the needle-like recessed portions are formed on the mold. Accordingly, it is possible to stably produce a transdermal absorption sheet in a state in which the shape of the transdermal absorption sheet is maintained. The expression "the polymer layer forming solution is supplied at a height equal to or higher than the height of the step portion" means that the polymer layer forming solution is supplied at a height equal to or higher than a surface flushed with the step portion in the periphery of the region in which the needle-like recessed portions are formed.

In another aspect of the present invention, it is preferable that in the polymer layer forming solution supply step, the polymer layer forming solution is supplied at a height higher than the height of the step portion in a range of greater than the step portion as seen from above and then a contact position of the polymer layer forming solution and the mold is fixed to the step portion while reducing the polymer layer forming solution.

According to the aspect, since the polymer layer forming solution is supplied at a height higher than the height of the step portion of the mold in a range of greater than the step portion and then the supplied polymer layer forming solution is fixed to the step portion while reducing the polymer layer forming solution, the polymer layer forming solution can be prevented from being repelled in the region in which the needle-like recessed portions are formed on the mold. Accordingly, it is possible to stably produce a transdermal absorption sheet in a state in which the shape of the transdermal absorption sheet is maintained. The expression "a contact position of the polymer layer forming solution and the mold" refers to the periphery of the liquid droplets of the polymer layer forming solution at the time of reduction of the polymer layer forming solution toward the region in which the needle-like recessed portions are formed, and the expression "contact position is fixed to the to the step portion" means that the periphery of the liquid droplets of the polymer layer forming solution is fixed to the upper side of the step portion. In addition, the reduction of the polymer layer forming solution is preferably performed by using surface tension.

In another aspect of the present invention, it is preferable that the height of the step portion of the mold is 10 μm or more and 5,000 μm or less.

In the aspect, the height of the step portion of the mold is defined and the amount of the polymer layer forming solution to be supplied can be reduced by setting the height of the step portion to the above range. Thus, the time for the polymer layer forming solution drying step can be shortened and production costs can be reduced.

In another aspect of the present invention, it is preferable that in the polymer layer forming solution supply step, a thickness of the polymer layer forming solution is 5,000 μm or less.

In the aspect, the thickness of the polymer layer forming solution in the polymer layer forming solution supply step is defined. Since the amount of the polymer layer forming solution to be supplied can be reduced by setting the thickness of the polymer layer forming solution to the above range, the time for the polymer layer forming solution drying step can be shortened and production costs can be reduced. The expression "the thickness of the polymer layer forming solution" is a thickness from the region in which the needle-like recessed portions are formed after the polymer layer forming solution supply step is performed and is a thickness of the thickest portion of the polymer layer forming solution.

In another aspect of the present invention, it is preferable that the step portion is a frame that is installed to be separated from the mold.

According to the aspect, drug solution filling step and the drug solution drying step can be performed on a flat mold by forming the step portion by the frame, and thus each step can be effectively performed. In addition, a frame can be installed according to a transdermal absorption sheet to be produced.

In another aspect of the present invention, it is preferable that the step portion has a step in the mold itself.

According to the aspect, it is possible to stably supply the polymer layer forming solution by providing a step in the mold itself to form the step portion.

In another aspect of the present invention, it is preferable that the step portion has a tapered shape widening in a direction from the region in which the needle-like recessed portions are formed to an upper side in a vertical direction.

According to the aspect, the effect of defoaming bubbles mixed in the polymer layer forming solution is exhibited by forming the step portion in a tapered shape widening to the upper side. It is possible to prevent defects of the needle-like protruding portions in the peeling-off step and damage of the needle-like protruding portions at the time of puncture by defoaming bubbles mixed in polymer layer forming solution.

In order to achieve the above object, the present invention provides a method of producing a transdermal absorption sheet, comprising: a drug solution filling step of filling needle-like recessed portions of a mold having the needle-like recessed portions with a drug solution that is a polymer solution containing a drug; a drug solution drying step of drying the drug solution filling the needle-like recessed portions to form a drug layer containing the drug; a polymer layer forming solution supply step of supplying a polymer layer forming solution to the mold, the mold being provided with a step portion that is lower than a region in which the needle-like recessed portions are formed in a periphery of the region in which the needle-like recessed portions are formed, in a range of equal to or greater than the step portion as seen from above, and then fixing a contact position of the polymer layer forming solution and the mold to the step portion while reducing the polymer layer forming solution; and a polymer layer forming solution drying step of drying the polymer layer forming solution supplied to the mold to form a polymer layer.

According to the present invention, since the polymer layer forming solution for forming a polymer layer is supplied in a range equal to or greater than the step portion by providing the step portion that is lower than the region in which the needle-like recessed portions are formed in the periphery of the region in which the needle-like recessed portions are formed in the mold in which the needle-like recessed portions are formed and is fixed to the step portion by reduction, the polymer layer forming solution can be prevented from being repelled in the region in which the needle-like recessed portions are formed on the mold. Accordingly, it is possible to stably produce a transdermal absorption sheet in a state in which the shape of the transdermal absorption sheet is maintained. It is preferable that the polymer layer forming solution is reduced using the surface tension.

In another aspect of the present invention, it is preferable that in the polymer layer forming solution supply step, the polymer layer forming solution is supplied to each needle-like recessed portion in which the step portion is provided.

According to the aspect, it is possible to fix the supplied polymer layer forming solution to the respective step portions by supplying the polymer layer forming solution to each step portion.

In another aspect of the present invention, it is preferable that in the polymer layer forming solution supply step, a thickness of the polymer layer forming solution is 5,000 μm or less.

In the aspect, the thickness of the polymer layer forming solution in the polymer layer forming solution supply step is defined. Since the amount of the polymer layer forming solution to be supplied can be reduced by setting the thickness of the polymer layer forming solution to the above range, the time for the polymer layer forming solution drying step can be shortened and production costs can be reduced.

In another aspect of the present invention, it is preferable that the step portion has a step in the mold itself.

According to the aspect, it is possible to stably supply the polymer layer forming solution by forming the step portion by providing a step in the mold itself.

In another aspect of the present invention, in the case in which the polymer layer forming solution is supplied, in order to make a contractile force of the polymer layer forming solution which works on the step portion installed on the mold uniform, a shape formed by the step portion in the periphery of the region in which the needle-like recessed portions are formed is preferably a hexagonal or higher polygonal shape in which all corners are formed at an angle of 120° or greater as the step is viewed from above, and more preferably a regular hexagonal or higher polygonal shape or a circular shape.

Since the polymer layer forming solution is isotropically reduced, the shape formed by the step portion is formed in a hexagonal or higher polygonal shape in which all corners are formed at an angle of 120° C. or greater, and preferably in a regular hexagonal or higher polygonal shape or a circular shape, and then the polymer layer forming solution is reduced at the corner portions of the polygonal shape. Thus, it is possible to prevent the liquid droplets of the polymer layer forming solution from being dropped into the region in which the needle-like recessed portions are formed without fixing the polymer layer forming solution to the step portion. In the case in which the liquid droplets of the polymer layer forming solution are dropped into the region in which the needle-like recessed portions are formed, the polymer layer forming solution is repelled and the shape of the transdermal absorption sheet is not stable. Thus, this case is not preferable.

According to the method of producing a transdermal absorption sheet of the present invention, it is possible to stably maintain a liquid level even in a thin film with a simple apparatus configuration. In addition, it is possible to realize cost reduction by adopting a simple apparatus configuration.

BRIEF DESCRIPTION OF THE DRAWINGS

FIG. 5B is an illustration showing the reduction of the polymer layer forming solution according to the shape of the frame.

DESCRIPTION OF THE PREFERRED EMBODIMENTS

Hereinafter, a method of producing a transdermal absorption sheet of the present invention will be described with reference to the attached drawings. Incidentally, in the specification, numerical values indicated using the expression "to" mean a range including the numerical values indicated before and after the expression "to" as the lower limit and the upper limit.

(Transdermal Absorption Sheet)

Figure 1:
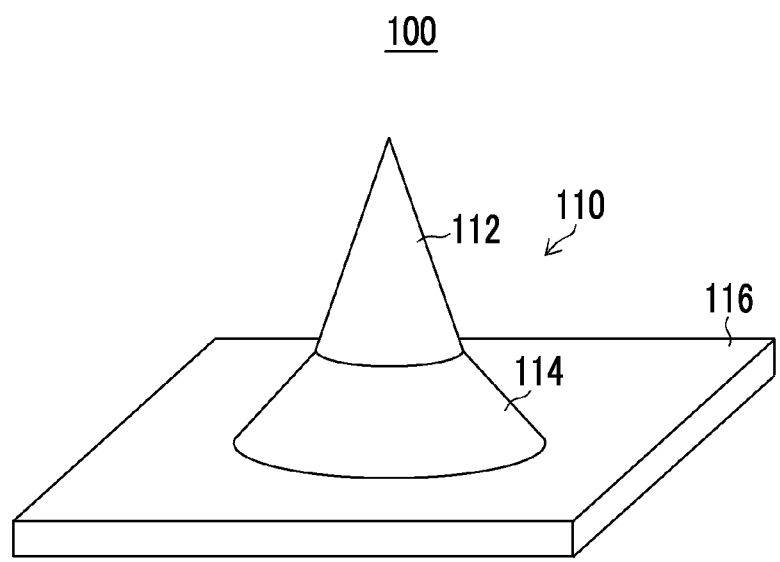
FIG. 1 is a perspective view showing a transdermal absorption sheet having a needle-like protruding portion.
Figure 2:
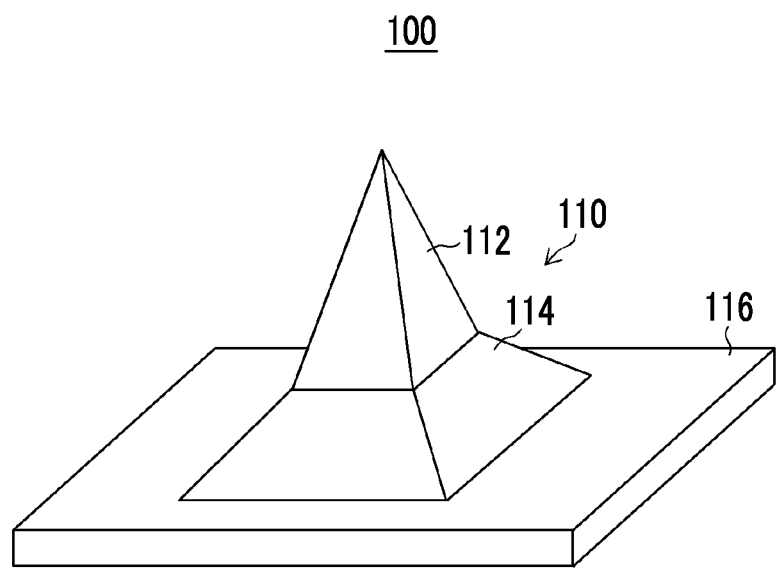
FIG. 2 is a perspective view showing a transdermal absorption sheet having a needle-like protruding portion of another shape.

A transdermal absorption sheet produced in the embodiment will be described. FIGS. 1 and 2 each show a needle-like protruding portion 110 (also referred to as a microneedle) that is a partially enlarged view of a transdermal absorption sheet 100.

The transdermal absorption sheet 100 delivers a drug into the skin by being attached to the skin. As shown in FIG. 1, the transdermal absorption sheet 100 has a tapered-shaped needle portion 112, a frustum portion 114 connected to the needle portion 112, and a plate-like sheet portion 116 connected to the frustum portion 114. The tapered-shaped needle portion 112 and the frustum portion 114 configure the needle-like protruding portion 110.

A plurality of frustum portions 114 is formed on the surface of the sheet portion 116 (only one frustum portion 114 is shown in FIG. 1). Out of the two end surfaces of the frustum portion 114, an end surface (lower base) having a larger area is connected to the sheet portion 116. Out of the two end surfaces of the frustum portion 114, an end surface (upper base) having a smaller area is connected to the needle portion 112. That is, out of the two end surfaces of the frustum portion 114, an end surface in a direction in which the end surface is separated from the sheet portion 116 has a smaller area. Since the end surface of the needle portion 112 having a large area is connected to the end surface of the frustum portion 114 having a small area, the needle portion 112 has a gradually tapered shape in a direction in which the needle portion is separated from the frustum portion 114.

In FIG. 1, the frustum portion 114 has a truncated cone shape, and the needle portion 112 has a cone shape. The shape of a tip end of the needle portion 112 can be appropriately changed to a curved surface having a radius of curvature of 0.01 μm or more and 50 μm or less, a flat surface, or the like in accordance with the degree of insertion of the needle portion 112 into the skin.

FIG. 2 shows a needle-like protruding portion 110 having another shape. In FIG. 2, the frustum portion 114 has a truncated square pyramid shape and the needle portion 112 has a quadrangular pyramid shape.

Figure 3:
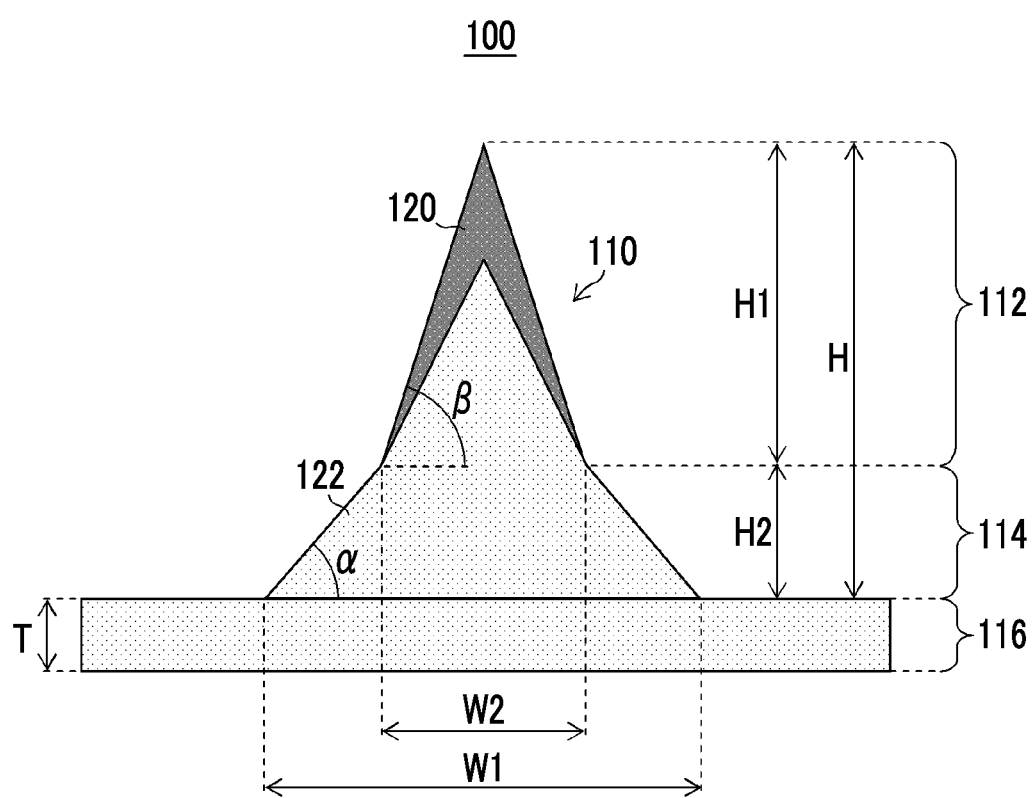
FIG. 3 is a cross-sectional view showing the needle-like protruding portions of the transdermal absorption sheets shown in FIGS. 1 and 2.

FIG. 3 shows cross-sectional views of the transdermal absorption sheets 100 shown in FIGS. 1 and 2, respectively. As shown in FIG. 3, the transdermal absorption sheet 100 is formed of a drug layer 120 containing a predetermined amount of a drug and a polymer layer 122. Here, the expression "containing a predetermined amount of a drug" means containing a drug large in an amount such that the effect of the drug is exhibited in the case in which the transdermal absorption sheet 100 punctures the body surface. The drug layer 120 containing a drug is formed at the tip end of the needle-like protruding portion 110 (the tip end of the needle portion 112). The drug can be effectively delivered into the skin by forming the drug layer 120 at the tip end of the needle-like protruding portion 110. Hereinafter, the expression "containing a predetermined amount of a drug" is referred to as "containing a drug" if necessary.

In the portion of the needle portion 112 excluding the drug layer 120, the polymer layer 122 is formed. The frustum portion 114 is formed of the polymer layer 122. The sheet portion 116 is formed of the polymer layer 122. The distribution of the drug layer 120 and the polymer layer 122 forming the needle portion 112, the frustum portion 114, and the sheet portion 116 can be appropriately set.

The thickness T of the sheet portion 116 is preferably in a range of 10 μm to 2,000 μm and more preferably in a range of 10 μm to 1,000 μm. A width W1 of the bottom surface (lower base) in which the frustum portion 114 and the sheet portion 116 are in contact with each other is preferably in a range of 100 μm to 1,500 μm and more preferably in a range of 100 μm to 1,000 μm. A width W2 of the bottom surface (upper base) in which the frustum portion 114 and the needle portion 112 are in contact with each other is preferably in a range of 100 μm to 1,500 μm and more preferably in a range of 100 μm to 1,000 μm. It is preferable that the width W1 and the width W2 satisfy the relationship of W1>W2 in the above numerical value range.

The height H of the needle-like protruding portion 110 is preferably in a range of 100 μm to 2,000 μm and more preferably in a range of 200 μm to 1,500 μm. In addition, H1/H2 that is a ratio between a height H1 of the needle portion 112 and a height H2 of the frustum portion 114 is preferably in a range of 1 to 10 and more preferably in a range of 1.5 to 8. In addition, the height H2 of the frustum portion 114 is preferably in a range of 10 μm to 1,000 μm.

An angle α formed between the side surface of the frustum portion 114 and a surface parallel with the surface of the sheet portion 116 is preferably in a range of 10° to 60° and more preferably in a range of 20° to 50°. In addition, an angle β formed between the side surface of the needle portion 112 and a surface parallel to the upper base of the frustum portion 114 is preferably in a range of 45° to 85° and more preferably in a range of 60° to 80°.

The angle β is preferably equal to or greater than the angle α. This is because the needle-like protruding portion 110 easily punctures the skin.

Figure 4:
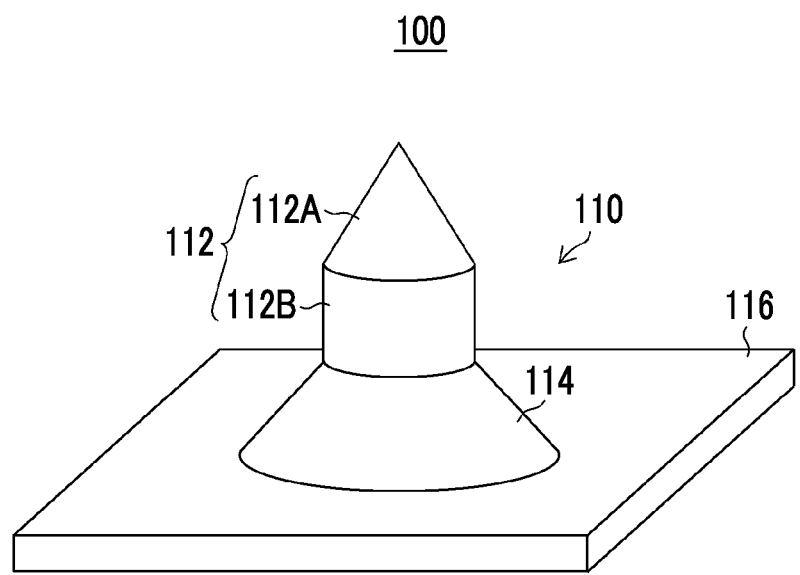
FIG. 4 is a perspective view showing a transdermal absorption sheet having a needle-like protruding portion of another shape.
Figure 5:
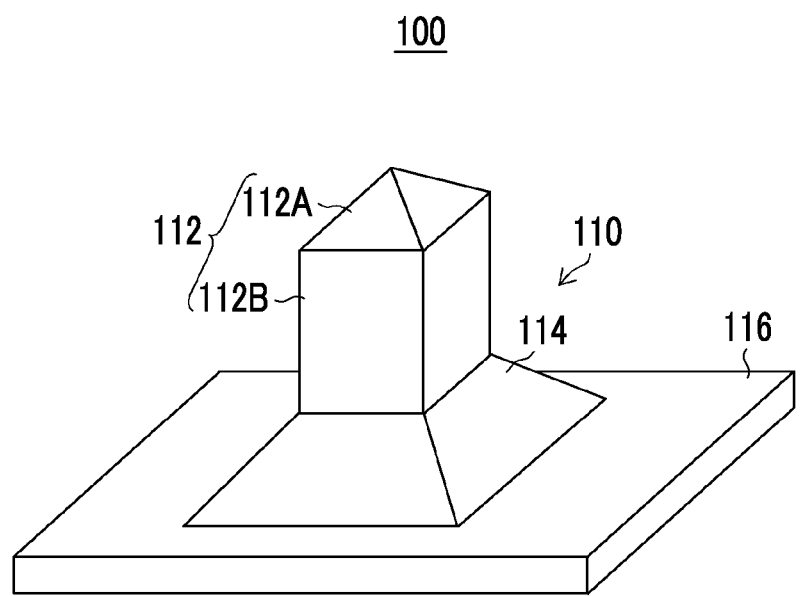
FIG. 5 is a perspective view showing a transdermal absorption sheet having a needle-like protruding portion of another shape.

FIGS. 4 and 5 show needle-like protruding portions 110 having other shapes. In the transdermal absorption sheets 100 shown in FIGS. 1 and 4 and the transdermal absorption sheets 100 shown in FIGS. 2 and 5, the frustum portions 114 have the same shape, and the needle portions 112 have different shapes. Each needle portion 112 shown in FIGS. 4 and 5 has a tapered needle-like portion 112A and a cylindrical body portion 112B. The bottom surface of the needle-like portion 112A is connected to an end surface of the body portion 112B. The other end surface that is not connected to the bottom surface of the needle-like portion 112A out of the end surfaces of the body portion 112B is connected to the upper base of the frustum portion 114.

The needle-like portion 112A shown in FIG. 4 has a conical shape and the body portion 112B has a columnar shape. The needle-like portion 112A shown in FIG. 5 has a quadrangular pyramid shape and the body portion 112B has a quadrangular shape.

Since the needle portion 112 has the body portion 112B, the needle portion 112 is formed to have a shape having a fixed cross-sectional area in a direction in which the needle portion is separated from the frustum portion 114. The tapered needle-like portion 112A of the needle portion 112 has a shape gradually tapered in a direction in which the needle portion is separated from the body portion 112B. The cylindrical body portion 112B has two facing end surfaces having almost the same area. The needle portion 112 has a tapered shape as a whole. According to a degree of insertion of the needle portion 112 into the skin, the shape of the tip end of the needle portion 112 can be appropriately changed to have a curved surface of a radius of curvature of 0.01 μm or more and 50 μm or less, a flat surface, or the like.

Figure 6:
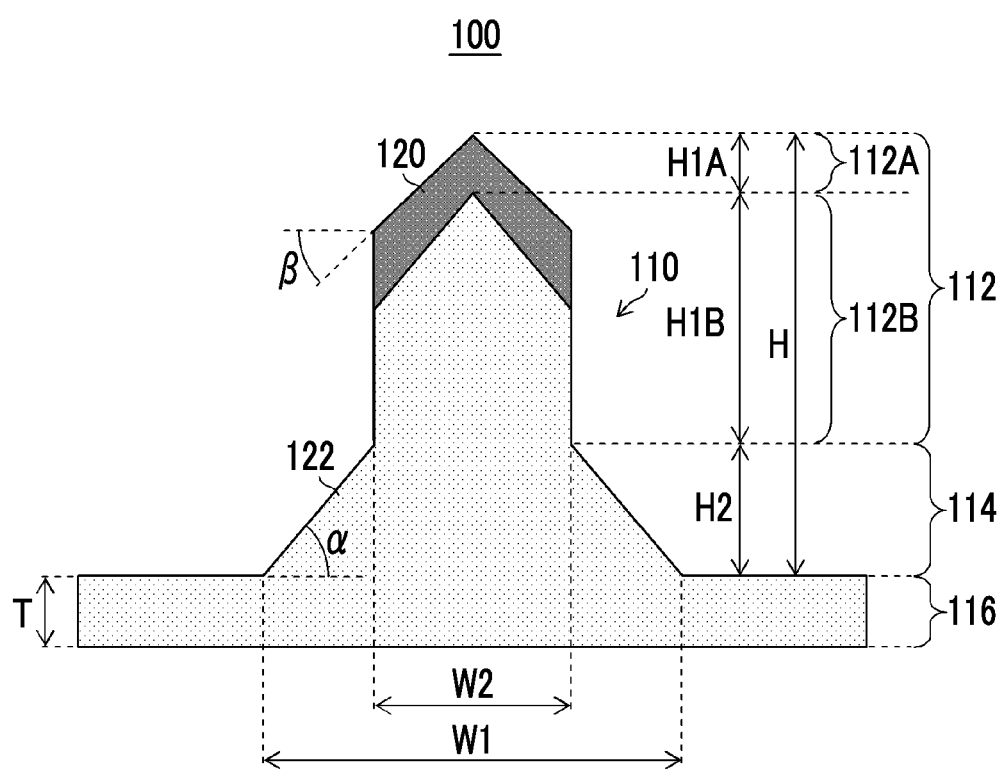
FIG. 6 is a cross-sectional view showing the needle-like protruding portions of the transdermal absorption sheets shown in FIGS. 4 and 5.

FIG. 6 is a cross-sectional view showing the transdermal absorption sheets 100 shown in FIGS. 4 and 5. As shown in FIG. 6, each transdermal absorption sheet 100 is formed of a drug layer 120 containing a drug and a polymer layer 122. The drug layer 120 containing a drug is formed at the tip end of the needle-like protruding portion 110 (the tip end of the needle portion 112). By forming the drug layer 120 at the tip end of the needle-like protruding portion 110, the drug can be effectively delivered into the skin.

In the portion of the needle portion 112 excluding the drug layer 120, the polymer layer 122 is formed. The frustum portion 114 is formed of the polymer layer 122. The sheet portion 116 is formed of the polymer layer 122. The distribution of the drug layer 120 and the polymer layer 122 forming the needle portion 112, the frustum portion 114, and the sheet portion 116 can be appropriately set.

The thickness T of the sheet portion 116, the width W1 of the lower base of the frustum portion 114, the width W2 of the upper base of the frustum portion 114, the height H of the needle-like protruding portion 110, and the height H2 of the frustum portion 114 can be set to be the same as the lengths in the transdermal absorption sheets 100 shown in FIG. 3. H1/H2 that is a ratio between the height H1 of the needle portion 112 and the height H2 of the frustum portion 114 can be set to be the same as the ratios in the transdermal absorption sheets 100 shown in FIG. 3.

H1B/H1A that is a ratio between a height H1A of the needle-like portion 112A and a height H1B of the body portion 112B is in a range of 0.1 or more and 4 or less and preferably in a range of 0.3 or more and 2 or less.

The angle α formed between the side surface of the frustum portion 114 and a surface parallel to the surface of the sheet portion 116 is in a range of 10° or greater and 60° or less and preferably in a range of 20° or greater and 50° or less. In addition, the angle β formed between the side surface of the needle-like portion 112A and an end surface parallel to the bottom surface of the body portion 112B is in a range of 45° or greater and 85° or less and preferably in a range of 60° or greater and 80° or less.

The angle β is preferably equal to or greater than the angle α. This is because the needle-like protruding portion 110 is easily inserted into the skin.

In the embodiment, the transdermal absorption sheets 100 having the needle portions 112 shown in FIGS. 1, 2, 4, and 5 are described but the shape of the transdermal absorption sheet 100 is not limited to these shapes.

(Mold)

Figure 7A:
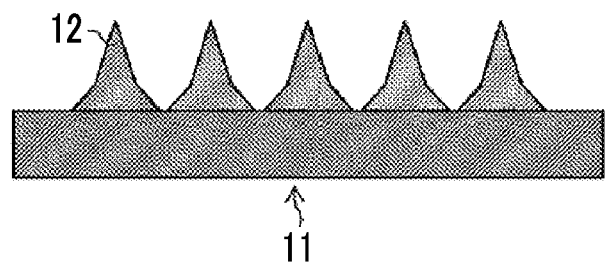
FIG. 7A is a step view of a method of producing a mold.
Figure 7B:
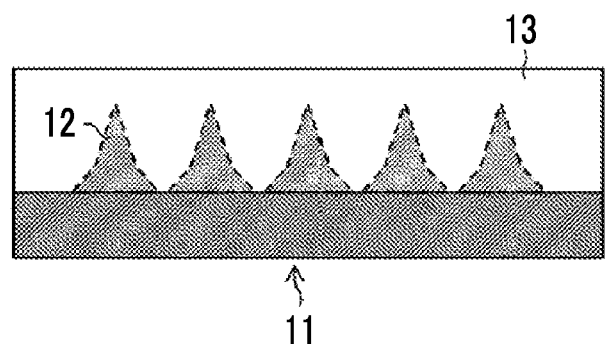
FIG. 7B is a step view of the method of producing the mold.
Figure 7C:
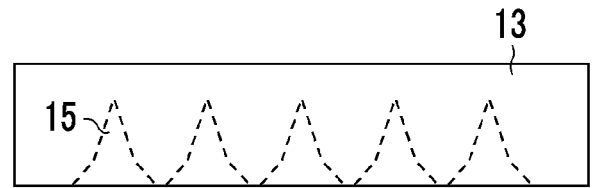
FIG. 7C is a step view of the method of producing the mold.

FIGS. 7A to 7C are step views showing a step of producing a mold (form).

As shown in FIG. 7A, first, an original plate for producing a mold for producing a transdermal absorption sheet is produced.

There are two kinds of methods of producing the original plate 11. The first method includes applying a photo resist to a Si substrate, and exposing and developing the photo resist. Then, etching by reactive ion etching (RIE) or the like is performed to produce a plurality of protruding portions 12, each having the same shape as the needle-like protruding portion of the transdermal absorption sheet, in arrays on the surface of the original plate 11. In addition, in the case of performing etching such as RIE to form the protruding portion 12 on the surface of the original plate 11, the protruding portion 12 can be formed by performing etching from an oblique direction while rotating the Si substrate.

As the second method, there is a method including processing a metal substrate of stainless steel, an aluminum alloy, Ni, or the like using a cutting tool such as a diamond bite to produce a plurality of protruding portions 12 in arrays on the surface of the original plate 11.

Next, as shown in FIG. 7B, a mold 13 is produced using the original plate 11. In order to produce a normal mold 13, a method using Ni electroforming or the like is generally used. Since the original plate 11 has the protruding portions 12 having a conical shape with a sharp tip end or a pyramid shape (for example, a quadrangular pyramid shape), the shape of the original plate 11 is accurately transferred to the mold 13, and the mold 13 can be peeled off from the original plate 11. Four methods that make possible to produce the mold 13 at a low cost are considered.

The first method is a method in which a silicone resin obtained by adding a curing agent to polydimethylsiloxane (PDMS, for example, SYLGARD (registered trademark) 184, manufactured by Dow Corning Corporation) is poured into the original plate 11 and cured by a heating treatment at 100° C., and then the mold 13 is peeled off from the original plate 11. The second method is a method in which an UV curable resin that is curable by ultraviolet irradiation is poured into the original plate 11 and irradiated with ultraviolet light in a nitrogen atmosphere, and then the mold 13 is peeled off from the original plate 11. The third method is a method in which a material obtained by dissolving a plastic resin such as polystyrene or polymethylmethacrylate (PMMA) in an organic solvent is poured into the original plate 11 which has been coated with a release agent, and is dried to volatilize the organic solvent for curing, and then the mold 13 is peeled off from the original plate 11. The fourth method is a method in which an inverted article is made by Ni electroforming.

In this manner, the mold 13 in which the needle-like recessed portions 15 having an inverted shape of the protruding portion 12 of the original plate 11 are arranged two-dimensionally is produced. The mold 13 produced in this manner is shown in FIG. 7C. In addition, in any of the above four methods, the mold 13 can be easily produced any number of times.

Figure 8A:
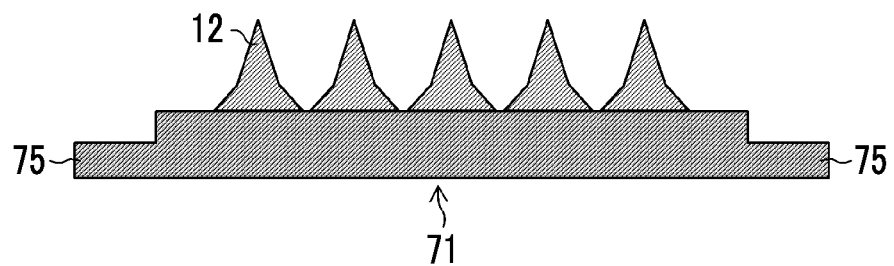
FIG. 8A is a step view of a method of producing a mold having another shape.
Figure 8B:
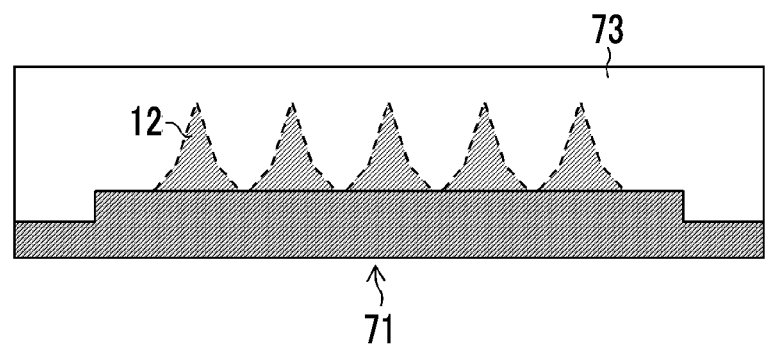
FIG. 8B is a step view of the method of producing the mold having another shape.
Figure 8C:
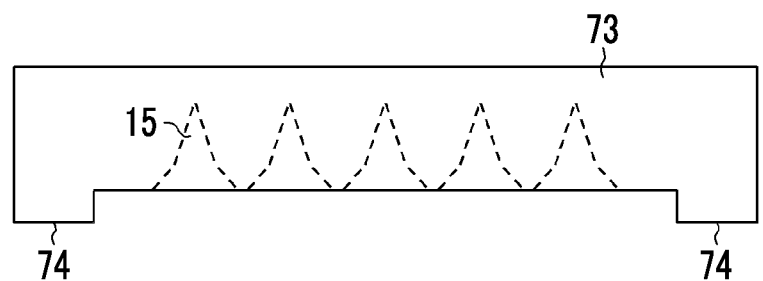
FIG. 8C is a step view of the method of producing the mold having another shape.

In the case of a mold itself having a step portion, a step portion is provided on the original plate to produce a mold having an inverted shape thereof. FIGS. 8A to 8C are step views of production of a mold 73 having a step portion 74 in which the periphery of a region in which the needle-like recessed portions 15 are formed is higher than a region in which the needle-like recessed portions 15 are formed.

Similar to the case of forming a mold not having a step portion, as shown in FIG. 8A, an original plate 71 for producing the mold 73 having the step portion 74 is produced. In the original plate 71, the step portion 75 is formed be lower than a region in which the protruding portions 12 are formed. The production of the original plate can be performed out in the same manner as in FIG. 7A.

Next, as shown in FIG. 8B, the mold 73 is produced by using the original plate 71. The production of the mold 13 can be performed out in the same manner as in FIG. 7B. Thus, as shown in FIG. 8C, the mold 73 in which the needle-like recessed portions 15 which are inverted shapes of the protruding portions 12 and the step portion 75 of the original plate 71 are arranged two-dimensionally and the step portion 74 is provided in the periphery thereof is produced.

Figure 9A:
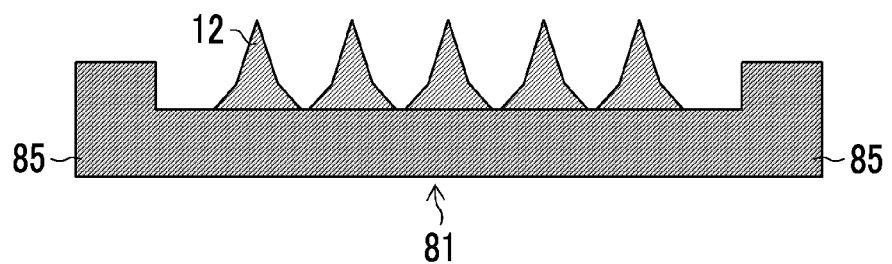
FIG. 9A is a step view of a method of producing a mold having another shape.
Figure 9B:
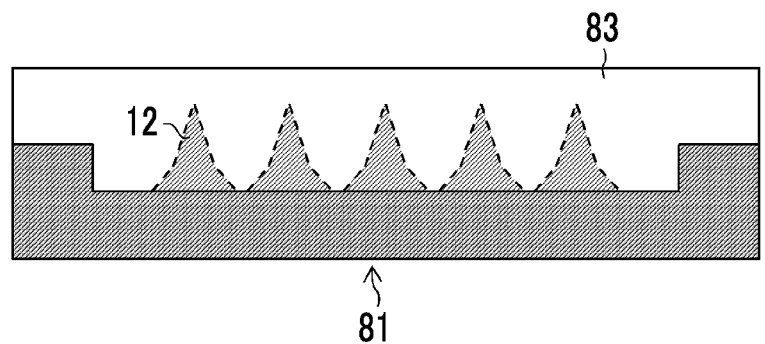
FIG. 9B is a step view of the method of producing the mold having another shape.
Figure 9C:
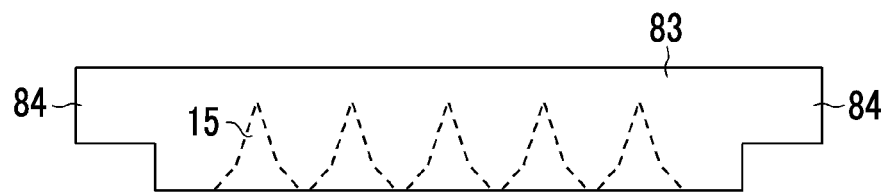
FIG. 9C is a step view of the method of producing the mold having another shape.

In addition, FIGS. 9A to 9C are step view of production of a mold 83 having a step portion 84 that is formed to lower than the region in which the needle-like recessed portions 15 are arranged two-dimensionally in the periphery of the region in which needle-like recessed portions 15 are formed.

Similar to FIGS. 7A and 8A, as shown in FIG. 9A, an original plate 81 for producing the mold 83 having a step portion 84 is produced. In the original plate 81, the step portion 85 is formed be higher than a region in which the protruding portions 12 are formed.

Next, as shown in FIG. 9B, the mold 83 is produced by using the original plate 81. Thus, as shown in FIG. 9C, the mold 83 in which the needle-like recessed portions 15 which are inverted shapes of the protruding portions 12 and the step portion 85 of the original plate 81 are arranged two-dimensionally and the step portion 85 is provided in the periphery thereof is produced. The method of producing the original plate and the method of producing the mold can be performed out in the same manner as in the production method of FIGS. 7A, 7B, 8A, and 8B.

Figure 10:
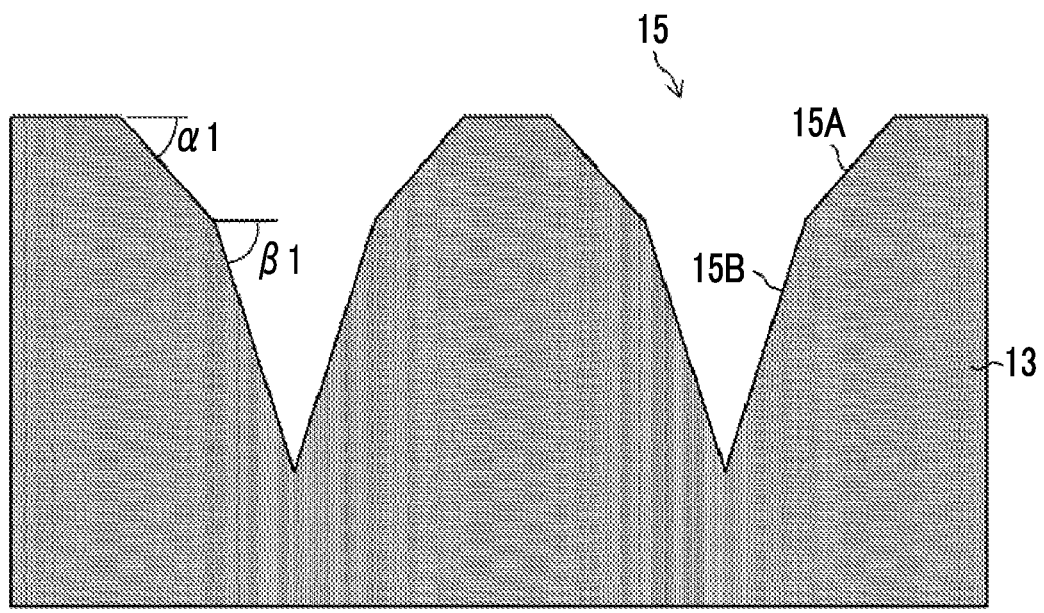
FIG. 10 is a partially enlarged view showing a mold.

FIG. 10 is a partially enlarged view showing the needle-like recessed portions 15 of the mold 13. In the molds 73 and 83, the needle-like recessed portions 15 have the same configuration. The needle-like recessed portion 15 is provided with a tapered inlet portion 15A that is narrower in a depth direction from the surface of the mold 13, and a tip end recessed portion 15B that is tapered in the depth direction. The angle α1 of the taper of the inlet portion 15A basically coincides the angle α formed between the side surface of the frustum portion and the sheet portion of the transdermal absorption sheet. In addition, the angle β1 of the taper of the tip end recessed portion 15B basically coincides the angle β formed between the side surface of the needle portion and the upper base of the frustum portion.

Figure 11:
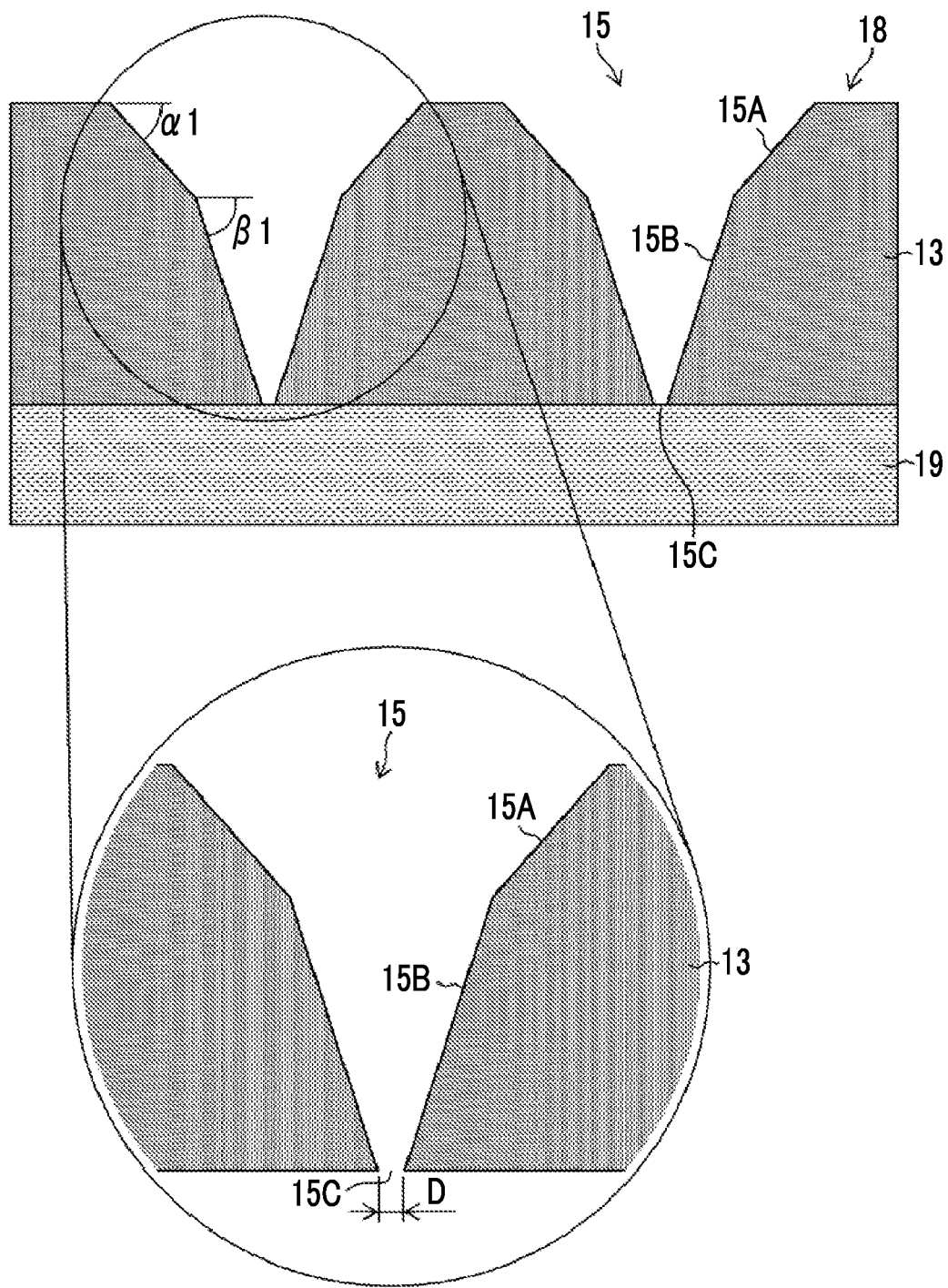
FIG. 11 is a partially enlarged view showing a mold.

FIG. 11 shows a more preferred embodiment of a mold complex 18 in performing a method of producing a transdermal absorption sheet. As shown in FIG. 11, the mold complex 18 includes a mold 13 in which a through-hole 15C is formed at the tip end of the needle-like recessed portion 15 and a gas permeable sheet 19 that is bonded to the through-hole 15C side of the mold 13 and is made of a material that is gas permeable, but is not liquid permeable. Through the through-hole 15C, the tip end of the needle-like recessed portion 15 communicates with the atmosphere through the gas permeable sheet 19. The expression "tip end of the needle-like recessed portion 15" means a side that is tapered in a depth direction of the mold 13 and is opposite to a side from which a drug solution and a polymer layer forming solution are poured.

Using such a mold complex 18, only the air present in the needle-like recessed portion 15 can be removed from the needle-like recessed portion 15 via the through-hole 15C without permeation of the transdermal absorption material solution filling in the needle-like recessed portion 15. The transferability in the case in which the shape of the needle-like recessed portion 15 is transferred to the transdermal absorption material is improved, and thus it is possible to form a sharper needle-like protruding portion.

The diameter D of the through-hole 15C is preferably in a range of 1 to 50 μm. By adjusting the diameter within this range, air bleeding is easily performed, and the tip end portion of the needle-like protruding portion of the transdermal absorption sheet can be formed into a sharp shape. As the gas permeable sheet 19 made of a material that is gas permeable, but is not liquid permeable, for example, PORE-FLON (product name, manufactured by Sumitomo Electric Industries, Ltd.) can be suitably used.

As the material used for the mold 13, a resin-based raw material and a metallic raw material can be used. Of these, a resin-based raw material is preferable and a raw material with high gas permeability is more preferable. The oxygen permeability, which is representative of the gas permeability, is preferably more than $1\times10^{-12}$ (mL/s·m·Pa) and more preferably more than $1\times10^{-10}$ (mL/s·m·Pa). By setting the gas permeability to be in the above range, the air present in the needle-like recessed portion 15 of the mold 13 can be removed from the mold 13. It is possible to produce a transdermal absorption sheet with few defects. As a resin-based raw material for such a material, general engineering plastics such as silicone resin, epoxy resin, polyethylene terephthalate (PET), polymethyl methacrylate (PMMA), polystyrene (PS), polyethylene (PE), polyacetal or polyoxymethylene (POM), polytetrafluoroethylene (PTFE), UV (ultraviolet) curable resin, phenolic resin, urethane resin, and the like can be used. In addition, examples of the metallic raw material include Ni, Cu, Cr, Mo, W, Ir, Tr, Fe, Co, MgO, Ti, Zr, Hf, V, Nb, Ta, α-aluminum oxide, stainless steel, and alloys thereof. In addition, since it is necessary to fix a polymer layer forming solution to the step portion in a polymer layer forming solution supply step as described later, the mold 13 is preferably formed by using a material with controlled water repellency and wettability. For example, the contact angle between the mold and the polymer layer forming solution is preferably greater than 90° and close to 90°.

(Polymer Solution)

The polymer solution that is a solution of the polymer resin used in the embodiment is described.

In the embodiment, the expression "polymer solution containing a predetermined amount of a drug" is referred to as a polymer solution containing a drug or a solution containing a drug, if necessary. Also, the expression "polymer solution containing a predetermined amount of a drug" is referred to as a drug solution. Whether or not a predetermined amount of a drug is contained in the solution can be determined based on whether or not the effect of the drug can be exhibited in the case in which the transdermal absorption sheet punctures the body surface. Accordingly, the expression "containing a predetermined amount of drug" means containing the drug in such an amount that the effect of the drug is exhibited in the case in which the transdermal absorption sheet punctures the body surface.

As the raw material for the resin polymer used for the polymer solution, a biocompatible resin is preferably used. It is preferable to use, as such a resin, sugar such as glucose, maltose, pullulan, chondroitin sulfate, sodium hyaluronate, or hydroxyethyl starch, protein such as gelatin, or a biodegradable polymer such as polylactic acid and a lactic acid-glycolic acid copolymer. Among these, gelatin-based raw materials can be suitably used since the gelatin-based raw materials have adhesiveness with many base materials and have a high gel strength as materials to be gelated, and in the peeling-off step described later, the raw materials can be closely attached to the base material and a polymer sheet can be peeled off from the mold using the base material. The concentration of the resin is preferably such that 10% to 50% by mass of the resin polymer is contained in the polymer solution for forming the polymer layer 122, while the concentration depends on the kind of the material. Additionally, a solvent used for dissolution may be other than hot water as long as the solvent has volatility, and methyl ethyl ketone (MEK), alcohol, or the like may be used. The drug to be supplied to the inside of the human body may concurrently be dissolved into the solution of the polymer resin in accordance with the application. The concentration of the polymer of the polymer solution containing a drug for forming the drug layer 120 (the concentration of the polymer excluding the drug in the case in which the drug itself is a polymer) is preferably 0% to 30% by mass.

For a method for preparing the polymer solution, in the case in which a water-soluble polymer (gelatin or the like) is used, the solution may be prepared by dissolving water-soluble powder into water, and after the dissolution, adding a drug to the solution or putting and dissolving water-soluble polymer powder into a drug-containing solution dissolved therein. In the case in which the polymer resin is difficult to dissolve into water, the polymer resin may be dissolved on heating. The temperature can be appropriately selected as needed depending on the kind of the polymer material, but the material is preferably heated at about 60° C. or lower. Regarding the viscosity of the solution of the polymer resin, the viscosity of the drug-containing solution for forming the drug layer 120 is preferably 100 Pa·s or less and more preferably 10 Pa·s or less. The viscosity of the solution for forming the polymer layer 122 is preferably 2,000 Pa·s or less and more preferably 1,000 Pa·s or less. Appropriate adjustment of the viscosity of the solution of the polymer resin facilitates injection of the solution into the needle-like recessed portions of the mold. For example, the viscosity of the solution of the polymer resin can be measured with a capillary type viscometer, a falling ball type viscometer, a rotational type viscometer, or an oscillatory type viscometer.

(Drug)

The drug that the polymer solution contains is not particularly limited as long as the drug is a substance having a function as a drug. Particularly, the drug is preferably selected from peptide, protein, nucleic acid, polysaccharide, a vaccine, a medical compound, and a cosmetic component. In addition, it is preferable that the medical compound belongs to a water-soluble low-molecular-weight compound.

(Method of Producing Transdermal Absorption Sheet)

Figure 12:
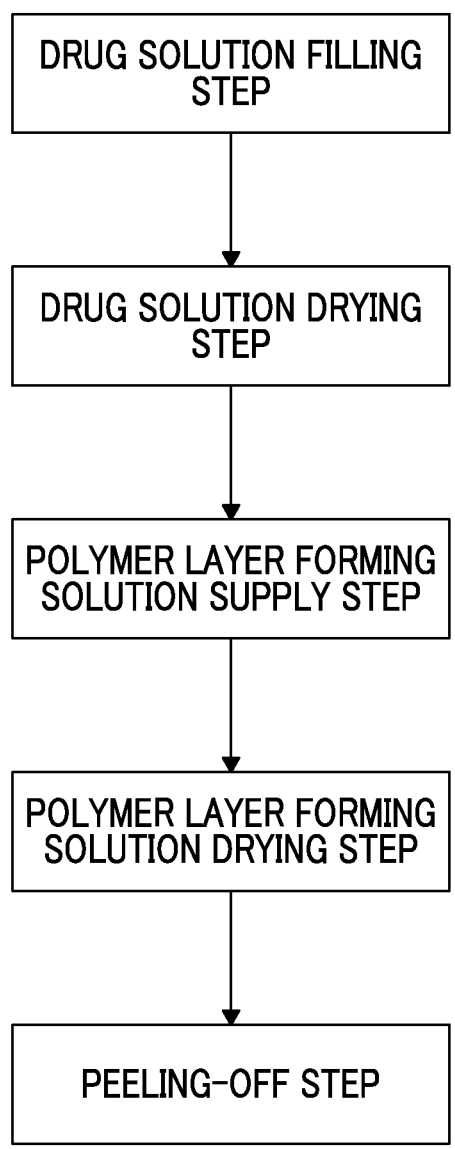
FIG. 12 is a flowchart of a method of producing a transdermal absorption sheet.

The method of producing the transdermal absorption sheet of the embodiment include at least five steps of a drug solution filling step, a drug solution drying step, a polymer layer forming solution supply step, a polymer layer forming solution drying step, and a peeling-off step in this order as shown in FIG. 12.

(Drug Solution Filling Step)

Figure 13A:
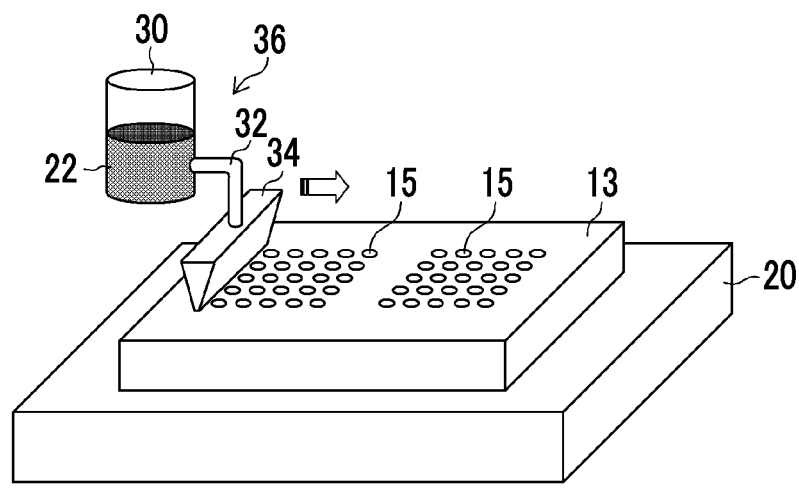
FIG. 13A is a schematic view showing a step of filling needle-like recessed portions of a mold with a drug solution.

The method of producing the transdermal absorption sheet using the mold 13 will be described. As shown in FIG. 13A, the mold 13 with the two-dimensionally arranged needle-like recessed portions 15 is placed on a base 20. Two sets of a plurality of needle-like recessed portions 15, each set including 5×5 two-dimensionally arranged needle-like recessed portions 15, are formed in the mold 13. A liquid supply apparatus 36 which has a liquid feed tank 30 storing a drug solution 22 that is a polymer solution containing a predetermined amount of a drug, a pipe 32 connected to the liquid feed tank 30, and a nozzle 34 connected to a tip end of the pipe 32 is prepared. The drug solution 22 is discharged from the tip end of the nozzle 34.

Figure 14:
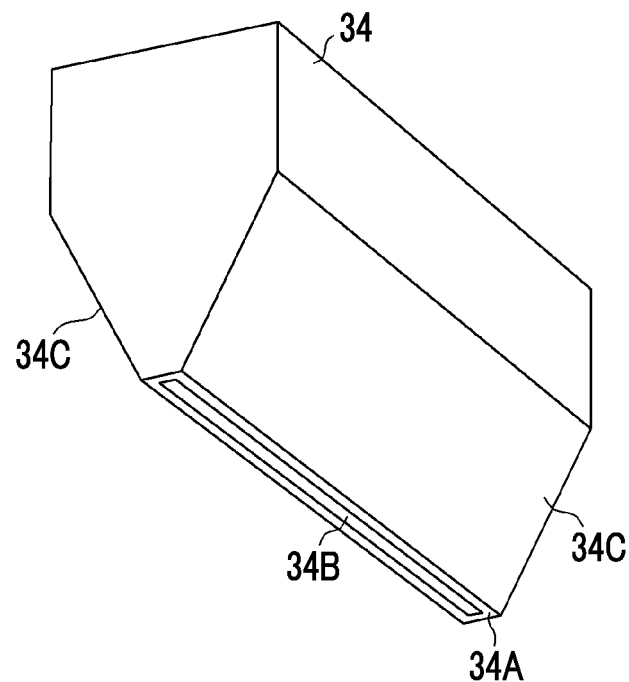
FIG. 14 is a perspective view showing a tip end of a nozzle.

FIG. 14 shows a schematic perspective view of the tip end portion of the nozzle. As shown in FIG. 14, the tip end of the nozzle 34 includes a lip portion 34A that has a flat surface on the tip end side, a slit-shaped opening portion 34B, and two inclined surfaces 34C that are widened along the lip portion 34A in a direction away from the opening portion 34B. The slit-shaped opening portion 34B, for example, allows a plurality of needle-like recessed portions 15 constituting one column to be simultaneously filled with the drug solution 22. The size (length and width) of the opening portion 34B is appropriately selected in accordance with the number of needle-like recessed portions 15 to be filled at a time.

An increased length of the opening portion 34B makes it possible to fill an increased number of needle-like recessed portions 15 with the drug solution 22 at a time. Thus, productivity can be improved.

Figure 15:
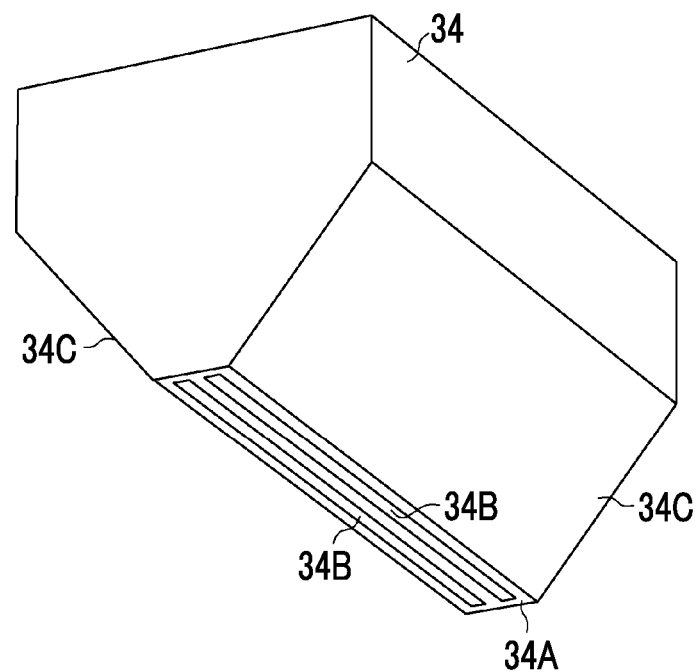
FIG. 15 is a perspective view showing a tip end of another nozzle.

FIG. 15 shows a schematic perspective view of a tip end portion of another nozzle. As shown in FIG. 15, the nozzle 34 has a lip portion 34A having a flat surface on the tip end side, two slit-shaped opening portions 34B, and two inclined surfaces 34C that are widened along the lip portion 34A in a direction away from the opening portion 34B. The two opening portions 34B, for example, allow a plurality of needle-like recessed portions 15 constituting two columns to be simultaneously filled with the drug solution 22 containing a drug.

As the material used for the nozzle 34, an elastic raw material and a metallic raw material may be used. For example, TEFLON (registered trademark), stainless steel (SUS), or titanium may be used.

Figure 13B:
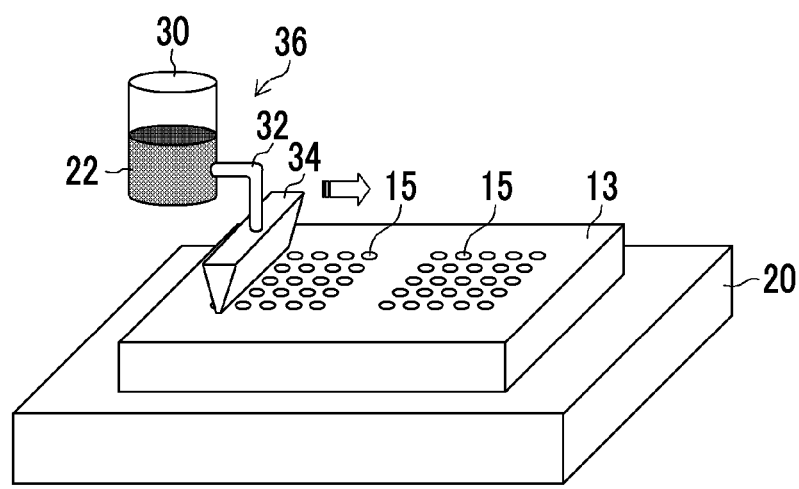
FIG. 13B is a schematic view showing the step of filling the needle-like recessed portions of the mold with the drug solution.

The filling step will be described with reference to FIG. 13B. As shown in FIG. 13B, the position of the opening portion 34B in the nozzle 34 is adjusted on the needle-like recessed portions 15. The lip portion 34A of the nozzle 34 is in contact with the surface of the mold 13 since the nozzle 34 that discharges the drug solution 22 is pressed against the mold 13. The drug solution 22 is supplied from the liquid supply apparatus 36 to the mold 13, and the needle-like recessed portions 15 are filled with the drug solution 22 through the opening portion 34B in the nozzle 34. In the embodiment, the plurality of needle-like recessed portions 15 constituting one column are simultaneously filled with the drug solution 22. However, the present invention is not limited to this configuration. The needle-like recessed portions 15 may be filled with the drug solution 22 one by one. In addition, by using the nozzle 34 shown in FIG. 15, the plurality of needle-like recessed portions 15 constituting the plurality of columns can be simultaneously filled with the drug solution 22 so that filling is performed on the plurality of columns at a time.

In the case in which the mold 13 is formed of a raw material having gas permeability, the drug solution 22 can be sucked by sucking from the back surface of the mold 13, thereby promoting filling of the inside of the needle-like recessed portions 15 with the drug solution 22.

Figure 13C:
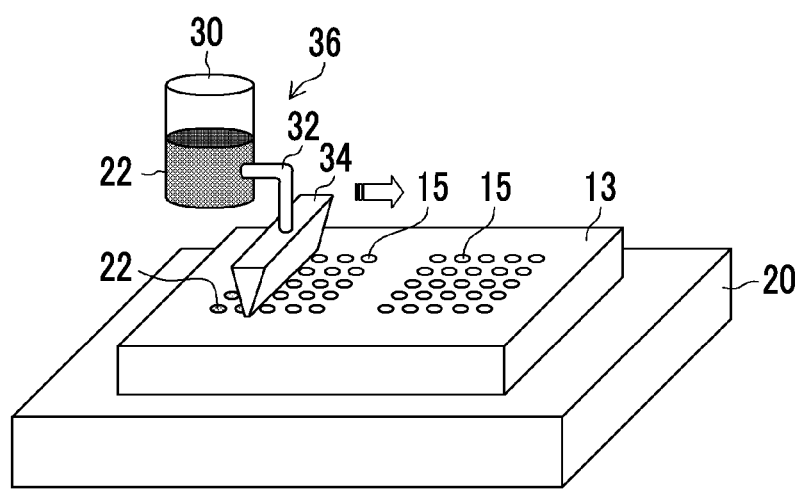
FIG. 13C is a schematic view showing the step of filling the needle-like recessed portions of the mold with the drug solution.

As shown in FIG. 13C, while bringing the lip portion 34A of the nozzle 34 into contact with the surface of the mold 13, the liquid supply apparatus 36 is relatively scanned in a direction perpendicular to a length direction of the opening portion 34B subsequent to the filling step in FIG. 13B. By scanning the surface of the mold 13 by the nozzle 34, the nozzle 34 is moved to the needle-like recessed portion 15 not filled with the drug solution 22. The position of the opening portion 34B of the nozzle 34 is adjusted on the needle-like recessed portions 15. The embodiment has been described with reference to the example in which the nozzle 34 is scanned. However, the mold 13 may be scanned.

Since the nozzle 34 is scanned on the surface of the mold 13 while the lip portion 34A of the nozzle 34 is brought into contact the surface of the mold 13, the nozzle 34 can scrape off the drug solution 22 remaining on the surface of the mold 13 excluding the needle-like recessed portions 15. This enables the drug solution 22 containing a drug to be prevented from remaining on the surface of the mold 13 excluding the needle-like recessed portions 15. In the embodiment, the inclined surfaces 34C of the nozzle 34 are arranged at a position perpendicular to the scanning direction indicated by the arrow. Accordingly, the nozzle 34 can be smoothly scanned on the surface of the mold 13.

In order to reduce damage to the mold 13 and to suppress deformation of the mold 13 due to compression as much as possible, the degree of pressurization of the nozzle 34 against the mold 13 in the case of scanning is preferably controlled. For example, the pressing force with which the nozzle 34 is pressed against the mold 13 or the pressing distance of the nozzle 34 against the mold 13 is preferably controlled. Furthermore, in order to prevent the drug solution 22 from remaining on the mold 13 excluding the needle-like recessed portions 15, at least one of the mold 13 or the nozzle 34 is desirably formed of a flexible, elastically deformable raw material.

The filling step shown in FIG. 13B and the scanning step shown in FIG. 13C are repeated to fill a 5×5 two-dimensionally arranged needle-like recessed portions 15 with the drug solution 22. In the case in which the 5×5 two-dimensionally arranged needle-like recessed portions 15 are filled with the drug solution 22, the liquid supply apparatus 36 is moved to the adjacent 5×5 two-dimensionally arranged needle-like recessed portions 15, and the filling step in FIG. 13B and the scanning step in FIG. 13C are repeated. The adjacent 5×5 two-dimensionally arranged needle-like recessed portions 15 are also filled with the drug solution 22.

The above filling step and scanning step may be in (1) a form in which the needle-like recessed portions 15 are filled with the drug solution 22 while the nozzle 34 is being scanned or (2) a form in which, while the nozzle 34 is in scanning, the nozzle 34 is temporarily stopped above the needle-like recessed portions 15 to fill the needle-like recessed portions 15 with the drug solution 22, and the nozzle 34 is scanned again after the filling. Between the filling step and the scanning step, the lip portion 34A of the nozzle 34 is pressed against the surface of the mold 13. The amount of the drug solution 22 discharged from the liquid supply apparatus 36 is preferably equal to the total volume of the plurality of needle-like recessed portions 15 of the mold 13 to be filled. The drug solution 22 is prevented from remaining on the surface of the mold 13 excluding the needle-like recessed portions 15 and thus wasting the drug can be reduced.

Figure 16:
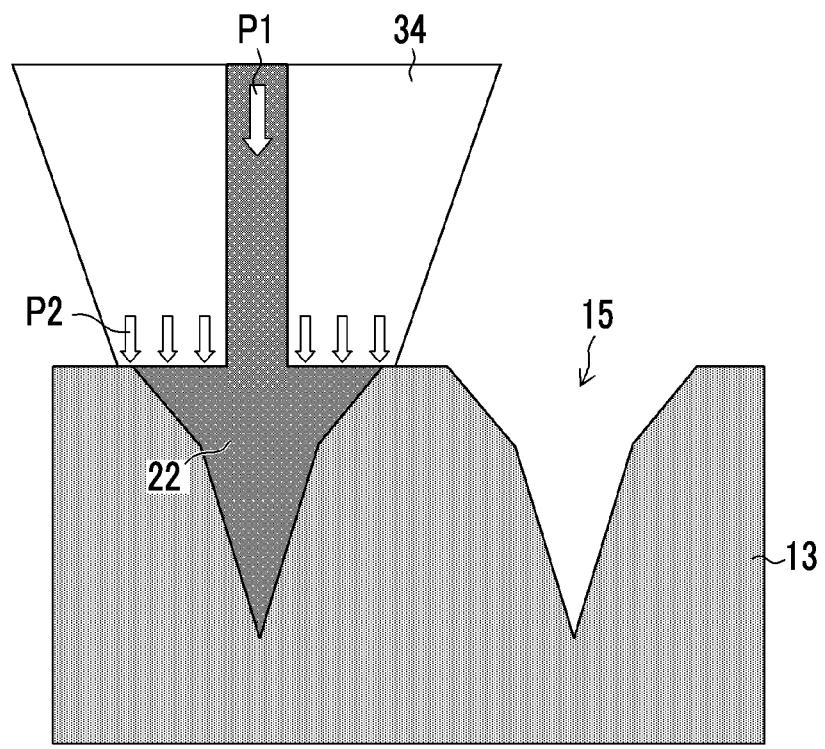
FIG. 16 is a partially enlarged view showing the tip end of the nozzle and the mold during filling.

FIG. 16 is a partially enlarged view of the tip end of the nozzle 34 and the mold 13 during filling of the needle-like recessed portions 15 with the drug solution 22. As shown in FIG. 16, filling of the inside of the needle-like recessed portions 15 with the drug solution 22 can be promoted by applying a pressuring force P1 into the nozzle 34. Moreover, in the case in which the needle-like recessed portions 15 is filled with the drug solution 22, a pressing force P2 with which the nozzle 34 is brought into contact with the surface of the mold 13 is preferably set to be equal to or greater than the pressuring force P1 in the nozzle 34. Setting the pressing force P2≥the pressuring force P1 enables the drug solution 22 to be restrained from leaking from the needle-like recessed portions 15 to the surface of the mold 13.

Figure 17:
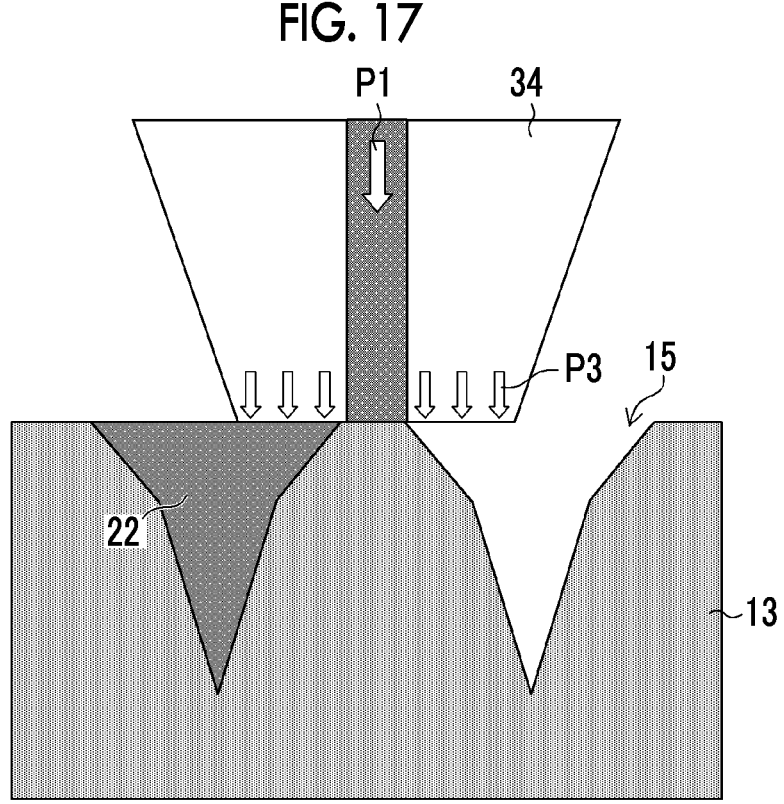
FIG. 17 is a partially enlarged view showing the tip end of the nozzle and the mold during scanning.

FIG. 17 is a partially enlarged view of the tip end of the nozzle 34 and the mold 13 during movement of the nozzle 34. In the case in which the nozzle 34 is scanned relative to the mold 13, a pressing force P3 with which the nozzle 34 is brought into contact with the surface of the mold 13 is preferably set to be smaller than the pressing force P2 with which the nozzle 34 is brought into contact with the surface of the mold 13 while filling is performed. This is intended to reduce damage to the mold 13 and to suppress deformation of the mold 13 associated with compression.

It is preferable that the lip portion 34A of the nozzle 34 is parallel to the surface of the mold 13. The posture of the nozzle 34 may be controlled by providing a joint driving mechanism at a mounting portion of the nozzle 34.

Figure 18:
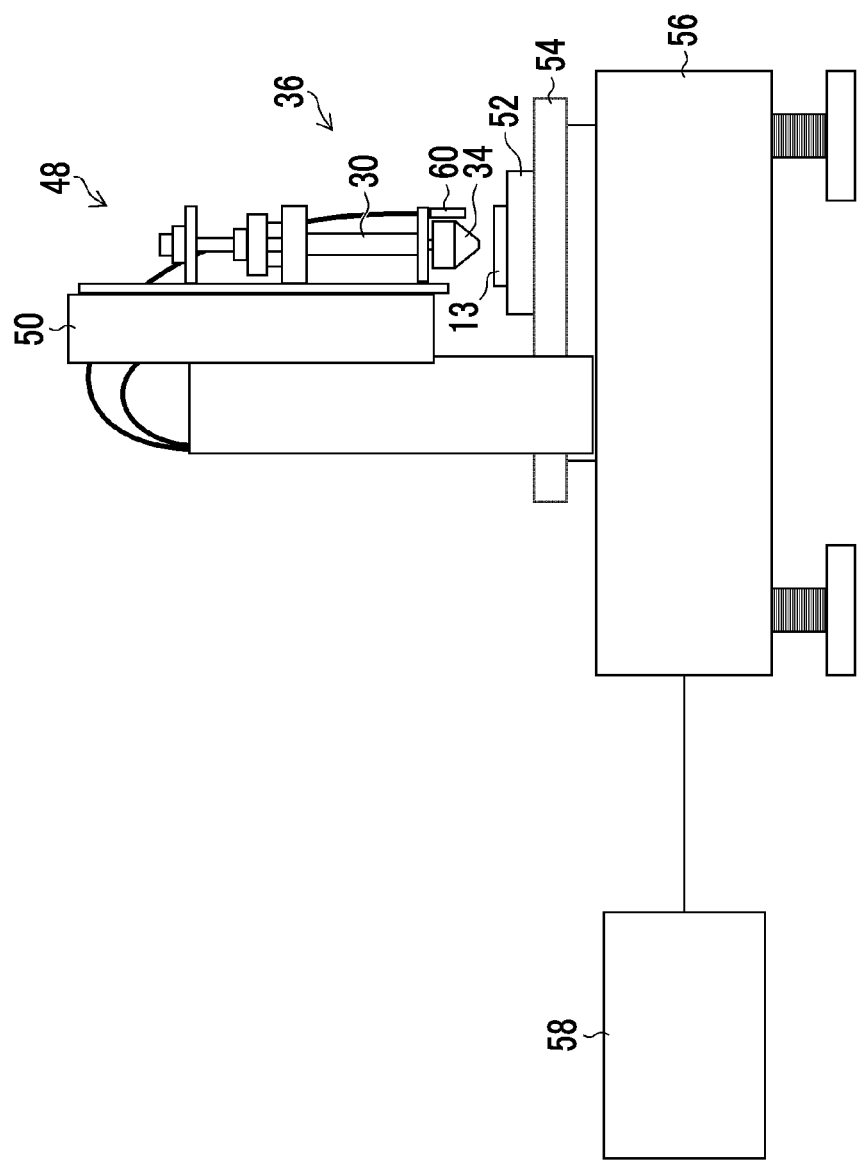
FIG. 18 is a schematic configuration view showing a drug solution filling apparatus.

The pressing force and/or the pressing distance of the nozzle 34 to the mold 13 is/are preferably controlled by driving the nozzle 34 in a Z-axis direction in accordance with the surface shape of the mold 13. FIG. 18 is a schematic configuration diagram of a drug solution filling apparatus 48 capable of controlling the pressing force and/or the pressing distance. The drug solution filling apparatus 48 has a liquid supply apparatus 36 that has a liquid feed tank 30 storing a drug solution and a nozzle 34 mounted on the liquid feed tank 30, a Z-axis driving unit 50 that drives the liquid feed tank 30 and the nozzle 34 in the Z-axis direction, a suction base 52 for placing the mold 13 thereon, a X-axis driving unit 54 that drives the suction base 52 in a X-axis direction, a stand 56 that supports the apparatus, and a control system 58.

The case of controlling a pressing force to be constant will be described. The Z-axis driving unit 50 brings the nozzle 34 close to the mold 13 up to Z-axis coordinates in which a desired pressing force is obtained. While the nozzle 34 brought into contact with the mold 13 is scanned by the X-axis driving unit 54, the drug solution 22 is discharged while Z-axis coordinate control is performed such that the pressing force becomes constant. The contact pressure measuring method is not particularly limited, but for example, various load cells can be used, for example, under the suction base 52 or in place of the suction base 52. The load cell means a measuring instrument capable of measuring a force for compression in a thickness direction. The pressing force is an arbitrary pressure within a range of 1 to 1,000 kPa with respect to the mold 13, and is preferably controlled to be constant.

The case of controlling a pressing distance to be constant will be described. Before contact with the nozzle 34, the surface shape of the mold 13 is measured in advance. While the nozzle 34 brought into contact with the mold 13 is scanned by the X-axis driving unit 54, the value obtained by performing Z-axis coordinate offset such that a desired pressing distance is provided with respect to the surface shape of the mold 13 is fed back to the Z-axis driving unit 50 by the control system 58. The drug solution 22 is discharged while feeding back the value.

The shape measuring method is not particularly limited. For example, an optical measuring instrument such as a non-contact-type laser displacement meter 60 or a contact-type probe-type step profiler can be used. Furthermore, the posture of the nozzle 34 in a slit direction may be controlled in accordance with the surface shape of the mold 13. The pressing distance is preferably controlled within a range of 1% to 15% with respect to the thickness of the mold 13. Through the operation with the control of the distance between the nozzle 34 and the mold 13 in the Z-axis direction by the Z-axis driving unit 50 in accordance with the shape of the mold 13, the compression deformation rate becomes uniform, and thus the accuracy of the filling amount can be improved.

Regarding the control of the pressing force and the pressing distance, the pressing force is preferably controlled in the case in which the pressing distance is small, and the pressing distance is preferably directly controlled in the case in which the pressing distance is large.

Figure 19:
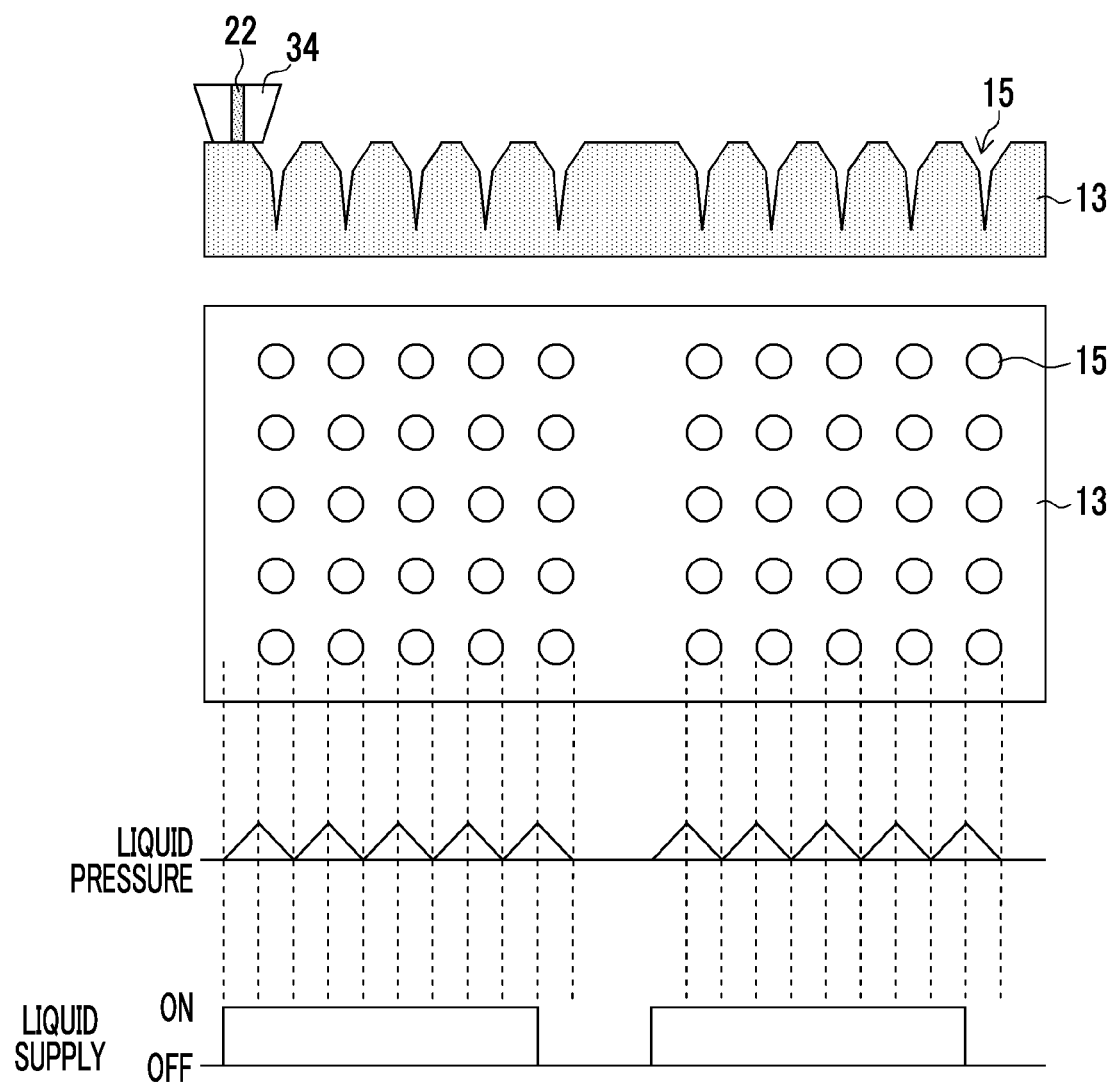
FIG. 19 is an illustration showing a relationship between the liquid pressure in the nozzle and the supply of a drug-containing solution.

FIG. 19 is an illustration showing the relationship between the liquid pressure in the nozzle and the supply of the drug-containing solution. As illustrated in FIG. 19, the supply of the drug solution 22 is started before the nozzle 34 is positioned above the needle-like recessed portions 15. The reason for this is to securely fill the needle-like recessed portions 15 with the drug solution 22. Until the filling of the plurality of needle-like recessed portions 15 of 5×5 is completed, the drug solution 22 is continuously supplied to the mold 13. The supply of the drug solution 22 to the mold 13 is stopped before the nozzle 34 is positioned above needle-like recessed portions 15 in the fifth column. Therefore, it is possible to prevent the drug solution 22 from overflowing from the needle-like recessed portions 15. The liquid pressure in the nozzle 34 increases in a region where the nozzle 34 is not positioned above the needle-like recessed portions 15 in the case in which the supply of the drug solution 22 is started. Meanwhile, in the case in which the nozzle 34 is positioned above the needle-like recessed portions 15, the needle-like recessed portions 15 are filled with the drug solution 22, and the liquid pressure in the nozzle 34 decreases. Such a change in the liquid pressure is repeated.

In the case in which the filling of the plurality of needle-like recessed portions 15 of 5×5 is completed, the nozzle 34 is moved to a plurality of adjacent needle-like recessed portions 15 of 5×5. Regarding the liquid supply, the supply of the drug solution 22 is preferably stopped in the case in which the nozzle is moved to the plurality of adjacent needle-like recessed portions 15 of 5×5. There is a distance between the needle-like recessed portions 15 in the fifth column and the needle-like recessed portions 15 in the next first column. In the case in which the drug solution 22 is continuously supplied therebetween during the scanning of the nozzle 34, the liquid pressure in the nozzle 34 may excessively increase. As a result, the drug solution 22 may flow to a region of the mold 13 excluding the needle-like recessed portions 15 from the nozzle 34. In order to suppress this problem, the supply of the drug solution 22 is preferably stopped.

The tip end of the nozzle 34 is preferably used after being cleaned in the case of performing filling with the drug solution 22. This is because the accuracy of the filling amount of the drug solution 22 is reduced in a case in which a substance adheres to the surface of the lip portion 34A of the nozzle 34 before filling. In general, wiping using non-woven cloth is performed for cleaning. During wiping, the cleaning can be effectively performed in the case in which non-woven cloth is permeated with water, a solvent, or the like.

After filling with the drug solution 22, there is a possibility that the drug solution 22 may remain on the surface of the mold 13 in the case in which the nozzle 34 is separated from the mold 13. By performing suck back control for suction of the drug solution 22 from the opening portion 34B of the nozzle 34 after completion of the filling of the needle-like recessed portions 15, an excessive amount of the drug solution 22 discharged can be sucked, and the liquid remaining on the surface of the mold 13 can thus be reduced.

In the drug solution filling step, the drug solution can be sucked from the through-hole 15C side using the mold complex 18 shown in FIG. 11 to fill the needle-like recessed portions 15 with the drug solution 22.

In the case in which the filling of the needle-like recessed portions 15 with the drug solution 22 is completed, the process proceeds to the drug solution drying step, the polymer layer forming solution supply step, the polymer layer forming solution drying step, and the peeling-off step.

Figure 20A:
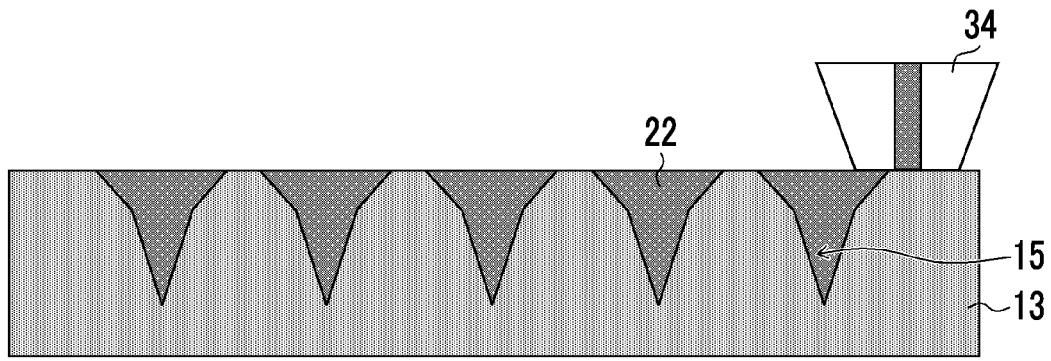
FIG. 20A is a schematic view showing a part of a step of producing a transdermal absorption sheet.

As shown in FIG. 20A, the needle-like recessed portions 15 of the mold 13 are filled with the drug solution 22 from the nozzle 34 in the drug solution filling step. The drug solution filling step is performed using the above-described method.

(Drug Solution Drying Step)

Figure 20B:
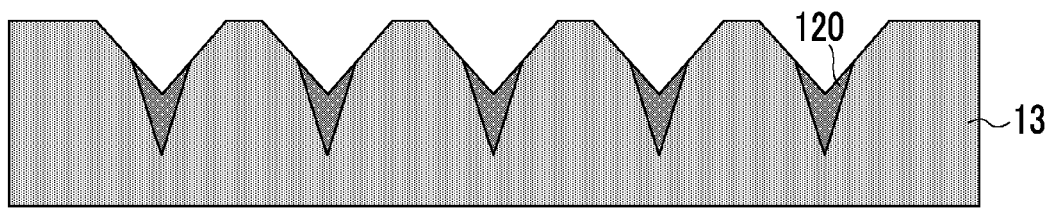
FIG. 20B is a schematic view showing a part of the step of producing the transdermal absorption sheet.

As illustrated in FIG. 20B, in the drug solution drying step, the drug solution 22 is dried and solidified, and thus a drug layer 120 containing a drug are formed in the needle-like recessed portions 15.

The drug solution drying step is a step of drying the drug solution 22 filling in the needle-like recessed portions 15 of the mold 13 and localizing the drug solution at the tip ends of the needle-like recessed portions 15. The drug solution drying step is preferably performed in an environment at a temperature of 1° C. or higher and 10° C. or lower. By performing the drug solution drying step in the above range, the occurrence of an air bubble defect can be reduced. In addition, the temperature and humidity condition for the drug solution drying step is controlled and the drying rate can be optimized. Thus, fixation of the drug solution 22 to the wall surface of the needle-like recessed portions 15 of the mold 13 can be reduced and solidification is performed while collecting the drug solution 22 at the tip ends of the needle-like recessed portions 15 by drying.

The drug solution 22 is preferably dried in a windless state in the drug solution drying step. Uneven drying occurs in the case in which the drug solution 22 is directly exposed to non-uniform wind. This is because, in a portion exposed to strong wind, the drying rate may be increased, the drug solution 22 may be fixed to the wall surface of the mold 13, and thus the localization of the drug solution 22 at the tip ends of the needle-like recessed portions 15 may be disturbed.

In order to realize the drying in a windless state, for example, a windshield is preferably installed. The windshield is installed so as not to directly expose the mold 13 to wind. As the windshield, a physical obstacle such as a lid, a hood, a screen, a fence, or the like is preferably installed since this is a simple method. In addition, in the case in which the windshield is installed, a vent hole or the like is preferably secured such that the installation space for the mold 13 is not in a sealed state. In the case in which the installation space is in a sealed state, water vapor in the sealed space may be saturated, and the drying of the drug solution 22 may not proceed. The vent hole is preferably formed such that the passage of vapor is possible, and is more preferably covered with a water vapor permeable film or the like to stabilize the air flow in the windshield. The drying time is appropriately adjusted in consideration of the shape of the needle-like recessed portion 15, the arrangement of the needle-like recessed portions 15, and the number of the needle-like recessed portions 15, the kind of the drug, the filling amount and the concentration of the drug solution 22, and the like.

The windless state refers to the case in which the wind speed is 0.5 m/s or less, including a state in which there is no wind at all. The reason for setting the wind speed to be in this range is that uneven drying rarely occurs.

In the drug solution drying step, the drug solution 22 is solidified by being dried, and is reduced compared with that in the case in which the filling with the drug solution 22 is performed. Accordingly, in the peeling-off step, the drug layer 120 can be easily peeled off from the needle-like recessed portion 15 of the mold 13.

(Polymer Layer Forming Solution Supply Step)

Figure 20C:
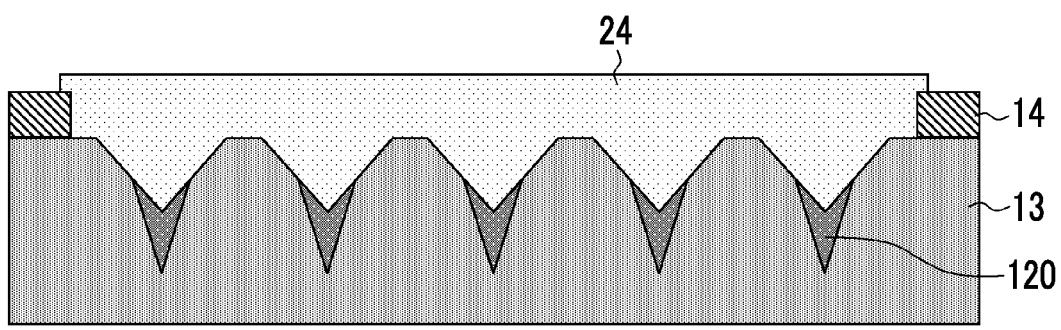
FIG. 20C is a schematic view showing a part of the step of producing the transdermal absorption sheet.

Next, as shown in FIG. 20C, the polymer layer forming solution 24 that is a polymer solution for forming the polymer layer 122 is supplied to the drug layer 120 containing a predetermined amount of a drug to fill the needle-like recessed portions 15 with the polymer layer forming solution 24. For the supply of the polymer layer forming solution, coating using a dispenser, bar coating, spin coating, coating using a spray, or the like can be applied but the method for the supply of the solution is not limited thereto. Hereinafter, an embodiment in which the polymer layer forming solution 24 is supplied to the mold 13 by coating will be described. Since the drug layer 120 containing a drug is solidified by being dried, diffusion of the drug contained in the drug layer 120 into the polymer layer forming solution 24 can be suppressed.

First Embodiment

Figure 21A:
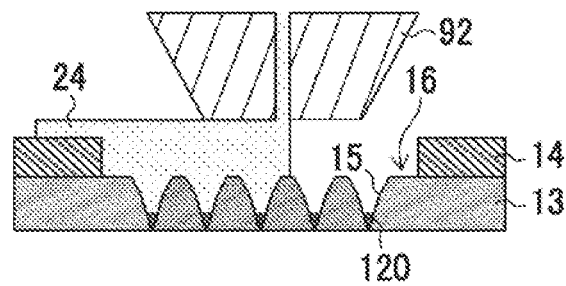
FIG. 21A is an illustration showing a polymer layer forming solution supply step according to a first embodiment.
Figure 21B:
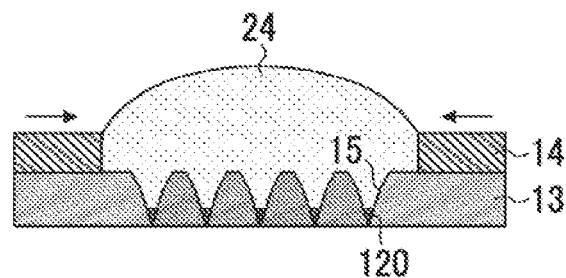
FIG. 21B is an illustration showing the polymer layer forming solution supply step according to the first embodiment.
Figure 21C:
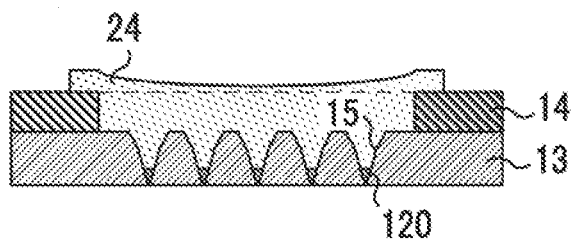
FIG. 21C is an illustration showing the polymer layer forming solution supply step according to the first embodiment.

FIGS. 21A and 21B are views illustrating a polymer layer forming solution supply step. In the polymer layer forming solution supply step according to the first embodiment, the frame 14 is installed in the periphery of a region 16 in which the needle-like recessed portions 15 are formed and the polymer layer forming solution 24 is applied to the mold 13 having a step portion higher than the region 16 in which the needle-like recessed portions 15 are formed. The frame 14 can be installed to be separated from the mold 13.

In the polymer layer forming solution supply step, as shown in FIG. 21A, the polymer layer forming solution 24 is applied using coating means 92 at a height equal to or higher than the step portion formed by the frame 14 installed in the periphery of the needle-like recessed portions 15 in a range of equal to or greater than the step portion as seen from above. The application of the polymer layer forming solution at a height equal to or higher than the height of the frame 14 means that the height of the polymer layer forming solution 24 in a part in which the polymer layer forming solution 24 and the frame 14 are in contact with each other is equal to or higher than the height of the frame 14. In order to easily peel off the produced transdermal absorption sheet, the frame 14 is formed of a material that easily repels the polymer layer forming solution, and after the application of the polymer layer forming solution 24, the polymer layer forming solution 24 is repelled by the frame 14 to be reduced by the surface tension. As shown in FIG. 21B, the contact position of the reduced polymer layer forming solution 24 and the mold 13 is fixed to the step portion of the frame 14. In a state in which the position is fixed by the frame 14, the shape of the polymer layer 122 of the transdermal absorption sheet (the shape of the sheet portion 116) can be stably formed by drying the polymer layer forming solution.

Figure 22A:
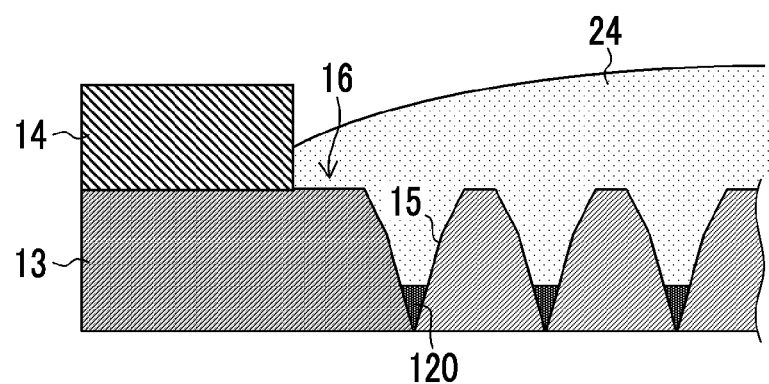
FIG. 22A is an illustration showing an unpreferable example of the polymer layer forming solution supply step.
Figure 22B:
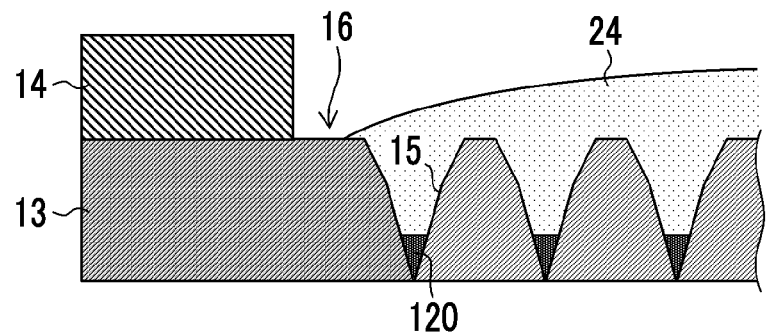
FIG. 22B is an illustration showing the unpreferable example of the polymer layer forming solution supply step.

FIGS. 22A and 22B are illustrations showing an unpreferable example of the polymer layer forming solution supply step. As shown in FIG. 22A, the polymer layer forming solution 24 is applied inside the frame 14 at a height lower than the height of the frame 14. After applying the solution, as shown in FIG. 22B, the polymer layer forming solution 24 is reduced by the surface tension in the region 16 in which the needle-like recessed portions 15 are formed. FIG. 22B shows a state after the polymer layer forming solution supply step is performed and since the volume of the polymer layer forming solution 24 is further reduced by a polymer layer forming solution drying step, a part in which the sheet portion 116 of the transdermal absorption sheet is unstably formed parts is generated.

As the material for the frame 14 provided on the mold 13, the same material as the material of the mold can be used. In addition, as the wettability with the polymer layer forming solution becomes higher, the liquid level at the time of drying can be made uniform and can be set to be in a gentle state. Thus, a local change in the liquid surface shape of the polymer layer forming solution can be prevented. In the present invention, since the polymer layer forming solution is repelled by the frame 14 and is fixed to the step portion by reduction, it is required for the material for forming the frame to have water repellency with respect to the polymer layer forming solution. Accordingly, a material for forming the frame of which the water repellency and wettability with respect to the polymer layer forming solution are controlled is preferably used and the contact angle between the frame and the polymer layer forming solution is preferably greater than 90° and close to 90°. The shape immediately after the polymer layer forming solution can be stably applied by using a material having good wettability with polymer layer forming solution as the material for the frame and entrainment of bubbles can be prevented. In addition, a liquid level strong and stable with respect to a disturbance such as wind or temperature unevenness at the time of drying can be fixed. On the other hand, in the case in which the wettability of the material for the frame and the polymer layer forming solution is poor, the liquid level of the coating liquid is a liquid level having a high curvature and a significant difference in surface tension is generated even with slight surface unevenness so that the coating liquid is deteriorated in shape and the coating liquid is repelled from the frame. Thus, this case is not preferable. In order to improve wettability, it is effective to make the raw material for the frame hydrophilic or to add a raw material having a surface active performance, such as protein, to the polymer layer forming solution. Further, the frame 14 may be installed from the drug solution filling step or may be installed before the polymer layer forming solution supply step.

The height of the frame 14 is preferably 10 μm or more and 5,000 μm or less. In order to fix the polymer layer forming solution 24 to the step portion, it is necessary to apply the polymer layer forming solution 24 at a height equal to or higher than the height of the frame 14 in a range of equal to or wider than the frame 14. Thus, setting the height of the frame 14 within this range allows a reduction in the amount of the polymer layer forming solution to be used. Accordingly, the drying time can be shortened. In the case in which the height of the frame 14 is lower than 10 μm, the polymer layer forming solution 24 is not fixed in the frame 14 and the mold 13 repels the polymer layer forming solution so that the sheet portion 116 is not formed or the like. Thus, there is a case in which a transdermal absorption sheet cannot be produced.

In the polymer layer forming solution supply step, the thickness of the polymer layer forming solution at the time of coating is preferably equal to or higher than the height of the frame 14 from the region 16 in which the needle-like recessed portions 15 are formed in the mold 13, and is 5,000 μm or less. In order to fix the polymer layer forming solution to the position of the frame 14, it is necessary to set the thickness of the polymer layer forming solution to be equal to or higher than the height of the frame 14. In the case in which the coating thickness of the polymer layer forming solution after the solution is applied is more than 5,000 μm, it takes some time for drying. While the liquid level is made thin as a whole to realize a reduction in drying load and a reduction in production costs, a film thickness distribution in which the film thickness in the vicinity of the frame is made thick and the film thickness in the vicinity of the center is made thin may be formed to stably fix the polymer layer to the frame.

Figure 23A:
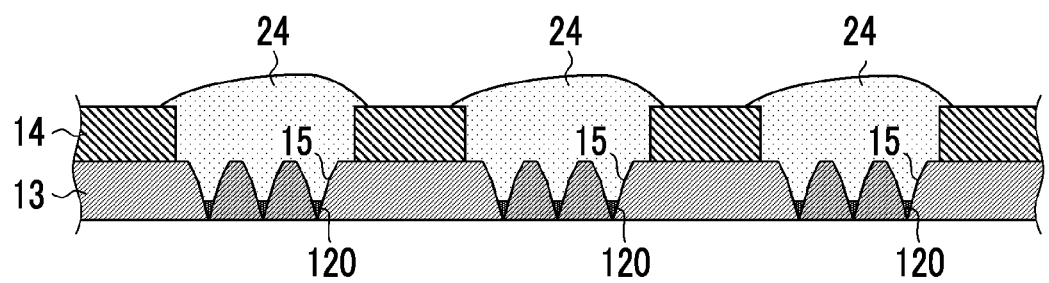
FIG. 23A is an illustration showing a method of applying a polymer layer forming solution to a mold.
Figure 23B:
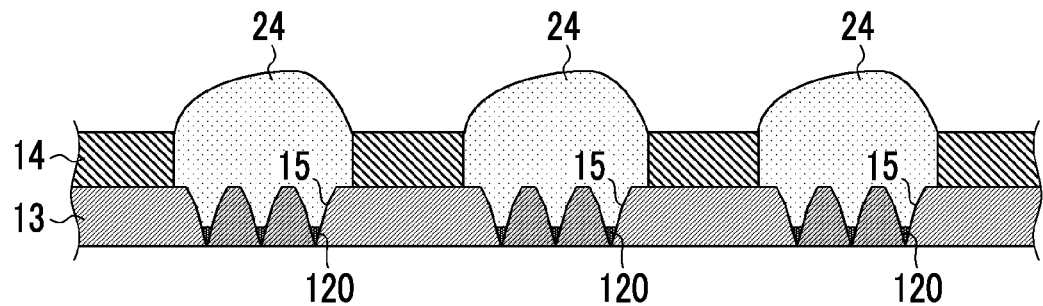
FIG. 23B is an illustration showing the method of applying the polymer layer forming solution to the mold.
Figure 24A:
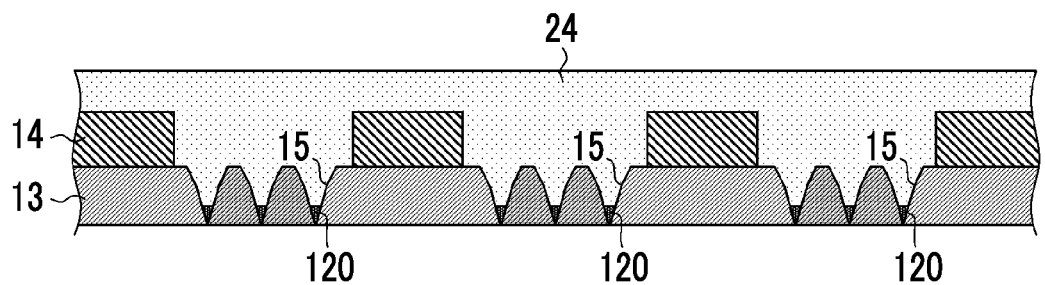
FIG. 24A is an illustration showing another method of applying a polymer layer forming solution to the mold.
Figure 24B:
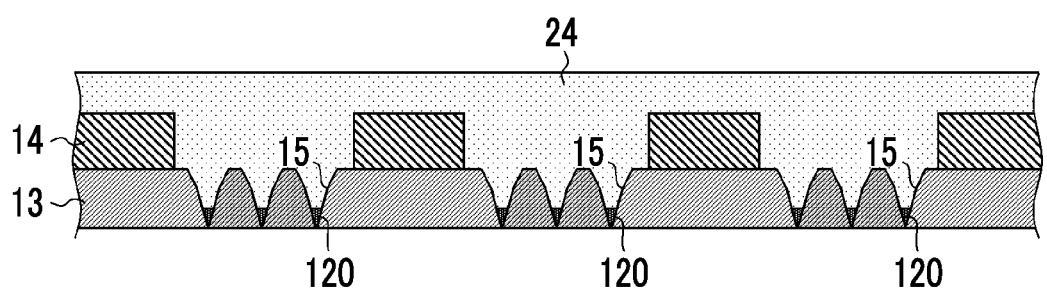
FIG. 24B is an illustration showing the another method of applying the polymer layer forming solution to the mold.
Figure 24C:
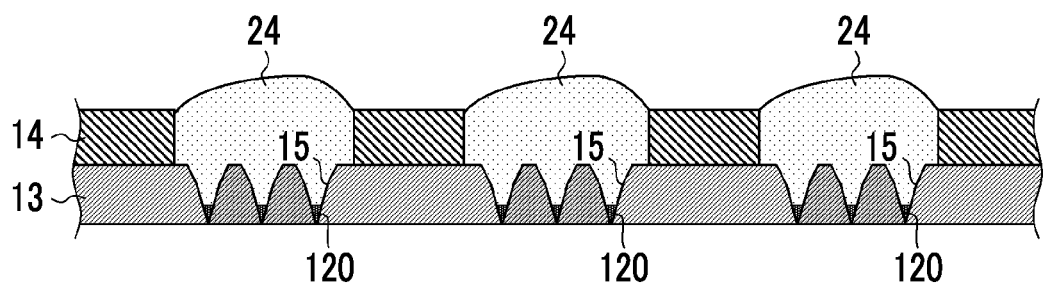
FIG. 24C is an illustration showing the another method of applying the polymer layer forming solution to a mold.

As the method of applying the polymer layer forming solution 24 to the mold 13, as shown in FIGS. 23A and 23B, the polymer layer forming solution may be applied to each needle-like recessed portion 15 surrounded by the frame 14 or as shown in FIGS. 24A to 24C, the polymer layer forming solution may be applied by covering the entire surface of the mold 13 with the frame 14. As shown in FIG. 23A, in the case in which the polymer layer forming solution 24 is applied to each frame 14, the polymer layer forming solution can be fixed in the frame 14 after the polymer layer forming solution is applied, as shown in FIG. 23B. The polymer layer forming solution can be applied to each frame 14 by intermittent stripe coating using a slit coater, using a dispenser, ink jetting, letterpress printing, lithographic printing, screening printing, or the like.

In addition, as shown in FIG. 24A, in the case in which the polymer layer forming solution is applied to the entire surface of the mold 13 and the amount of the polymer layer forming solution is large, as shown in FIG. 24B, in a state in which the polymer layer forming solution 24 is uniformly applied, the polymer layer forming solution drying step is performed. In this case, the polymer layer 122 can be stably formed in the next polymer layer forming solution drying step. In the case in which the amount of the polymer layer forming solution 24 is small, as shown in FIG. 24C, the polymer layer forming solution 24 is reduced toward the inside of the frame 14 (the region in which the needle-like recessed portions 15 are formed) and is fixed in the frame 14. Thus, a transdermal absorption sheet with a stable shape can be produced. As the method of uniformly applying polymer layer forming solution, general coating methods of using a slit coater, a slide coater, a blade coater, a hard coater, a roll coater, a gravure coater, a dip coater, a spray coater, and the like can be used.

Figure 25A:
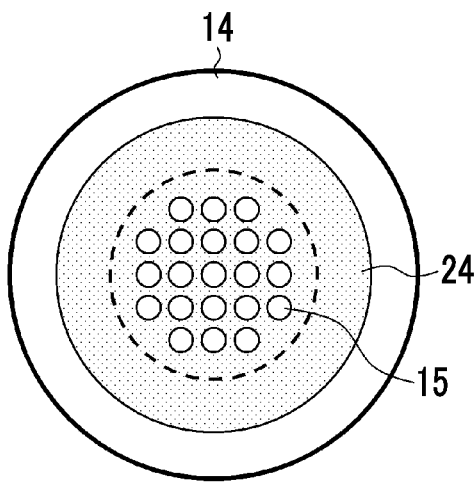
FIG. 25A is an illustration showing reduction of the polymer layer forming solution according to a shape of a frame.
Figure 25B:
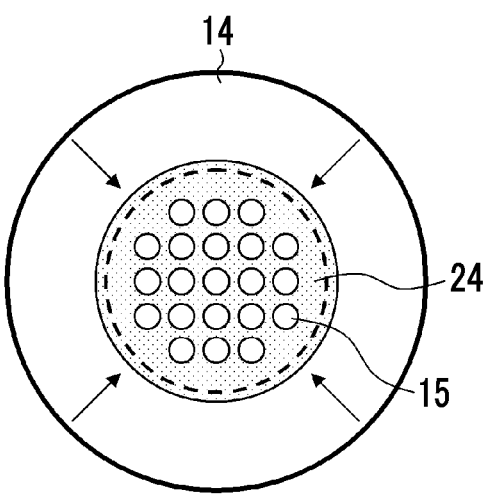
FIG. 25C is an illustration showing the reduction of the polymer layer forming solution according to the shape of the frame.
Figure 25C:
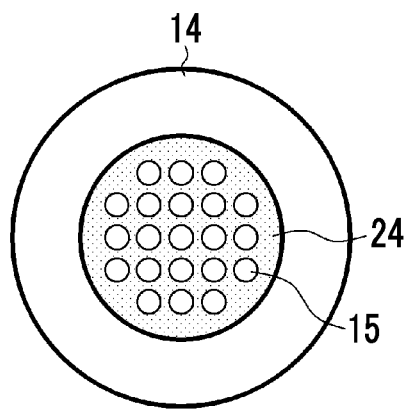

FIGS. 25A to 27C are illustrations showing the reduction of the polymer layer forming solution according to the shape of the frame. FIG. 25A is a view showing the case in which the polymer layer forming solution 24 is applied in a circular shape and the polymer layer forming solution 24 is applied using a circular frame 14. Since the polymer layer forming solution 24 is isotropically reduced as shown in FIG. 25B, as shown in FIG. 25C, the polymer layer forming solution 24 applied in a range wider than the frame 14 can be fixed to the position of the step portion formed by the frame 14.

Figure 26A:
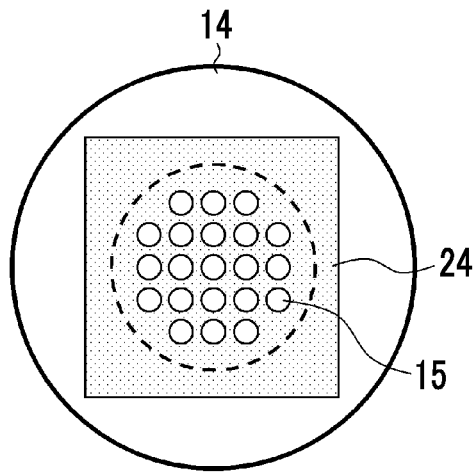
FIG. 26A is an illustration showing reduction of the polymer layer forming solution according to a shape of application.
Figure 26B:
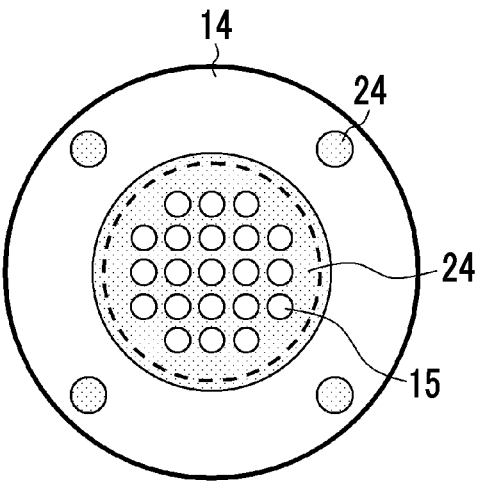
FIG. 26B is an illustration showing the reduction of the polymer layer forming solution according to the shape of the application.
Figure 26C:
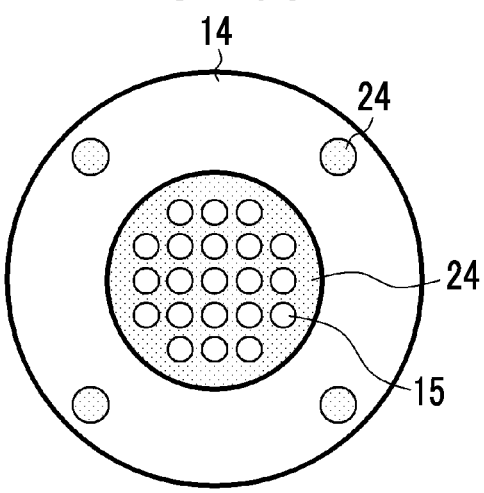
FIG. 26C is an illustration showing the reduction of the polymer layer forming solution according to the shape of the application.

FIG. 26A is a view in which the polymer layer forming solution 24 is applied in a quadrangular shape by using the circular frame 14. Even in the case in which the polymer layer forming solution 24 is applied in a quadrangular shape, as shown in FIG. 26B, the polymer layer forming solution 24 is isotropically reduced toward the step portion of the circular frame 14. As shown in FIG. 26C, while a repellent residue is present on the frame 14, the polymer layer forming solution 24 can be fixed to the position of the step portion formed by the frame 14.

Figure 27A:
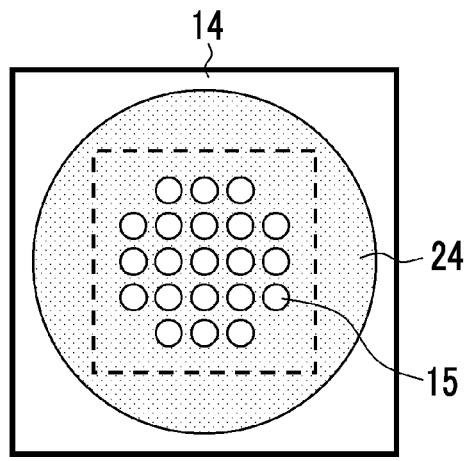
FIG. 27A is an illustration showing the reduction of the polymer layer forming solution according to another shape of a frame.
Figure 27B:
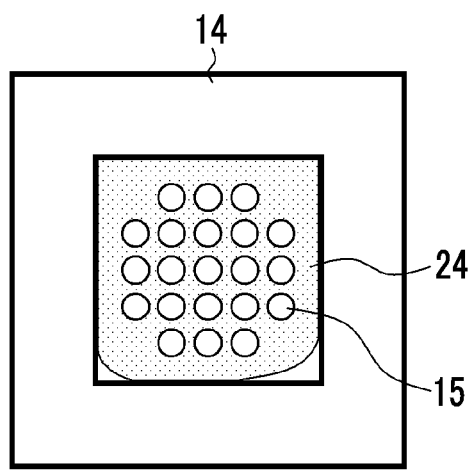
FIG. 27B is an illustration showing the reduction of the polymer layer forming solution according to the another shape of the frame.
Figure 27C:
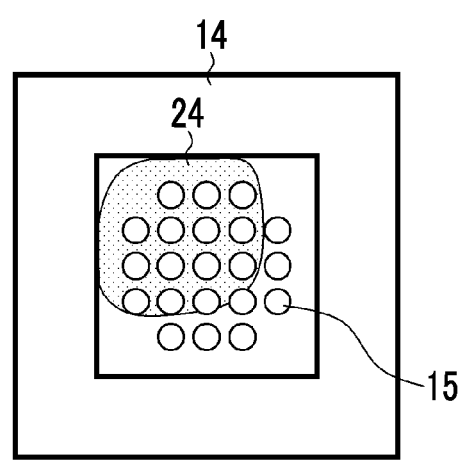
FIG. 27C is an illustration showing the reduction of the polymer layer forming solution according to the another shape of the frame.

FIG. 27A is a view in which the polymer layer forming solution 24 is applied in a circular shape by using a quadrangular frame 14. In the case in which the shape of the frame 14 is a quadrangular shape, isotropic reduction of the polymer layer forming solution 24 allows the polymer layer forming solution 24 to be fixed to the corner portions of the quadrangular frame 14 as shown in FIG. 27B. The polymer layer forming solution 24 may be detached from the frame 14. As shown in FIG. 27C, the polymer layer forming solution 24 detached from the frame 14 is further reduced on the mold and a polymer layer is not formed in a region in which the needle-like recessed portions 15 are formed. Thus, a transdermal absorption sheet may not be stably formed.

As shown in FIGS. 24A to 24C, in the case in which the polymer layer forming solution is uniformly applied to the mold, the polymer layer forming solution supply step can be performed without detachment of the polymer layer forming solution from the inside of the frame even in the case of the frame 14 having a quadrangular shape. In order to fix the polymer layer forming solution to the step portion formed by the frame, the shape of the periphery of the region in which the needle-like recessed portions are formed, which is formed by providing the frame, is preferably a hexagonal or higher polygonal shape in which all corners are formed at an angle of 120° or greater as seen from above, and is more preferably a regular hexagonal or higher polygonal shape, or a circular shape. By forming the shape of the step portion of the frame in the above shape, in the case of applying the polymer layer forming solution, a contractile force of the polymer layer forming solution by surface tension which works on the step portion installed on the mold can be made uniform. The expression "regular polygonal shape" is preferably a shape in which each side forming the polygonal is equal, but modification can be made within the range exhibiting the effect of the present invention.

Figure 28A:
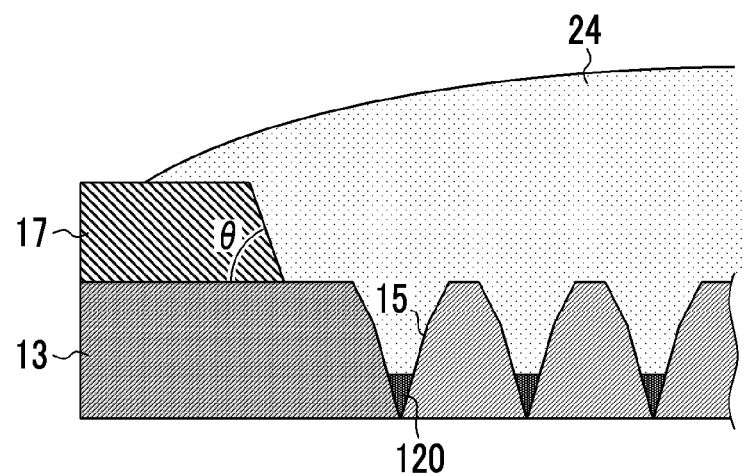
FIG. 28A is an illustration showing a polymer layer forming solution supply step using a frame having another shape.
Figure 28B:
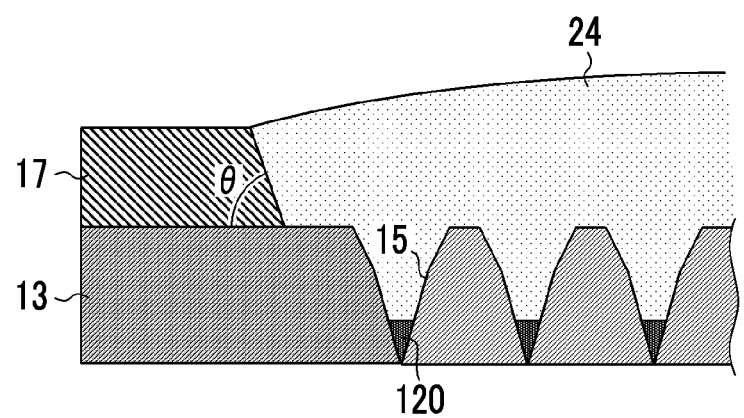
FIG. 28B is an illustration showing the polymer layer forming solution supply step using the frame having another shape.

FIGS. 28A and 28B are illustrations showing a polymer layer forming solution supply step by using a frame 17 having a tapered shape widening in a direction from the region in which the needle-like recessed portions are formed in the mold 13 to the upper side. Even in the case of using the tapered frame 17, the polymer layer forming solution 24 is applied in a range of equal to or wider than the region of the upper side of the frame 17 (FIG. 28A), and then is reduced by the surface tension. Thus, the polymer layer forming solution 24 can be fixed to the step portion formed by the frame 17 (FIG. 28B).

In addition, by forming the frame 14 in a tapered shape widening in a direction toward an upper side in a vertical direction, the effect of defoaming bubbles mixed in the polymer layer forming solution 24 is exhibited. Defoaming of bubbles mixed in the polymer layer forming solution 24 is performed and thus defects of the needle-like protruding portions in the peeling-off step and damage of the needle-like protruding portions at the time of puncture can be prevented.

For an angle θ of the taper of the frame 17, an angle formed between the frame and the mold 13 is preferably 45° or greater and 75° or less.

Modification Example

Figure 29A:
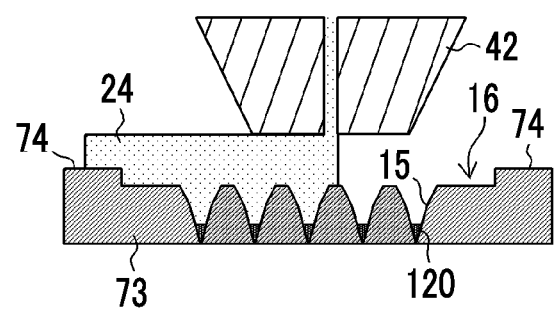
FIG. 29A is an illustration showing a polymer layer forming solution supply step according to a modification example of the first embodiment.
Figure 29B:
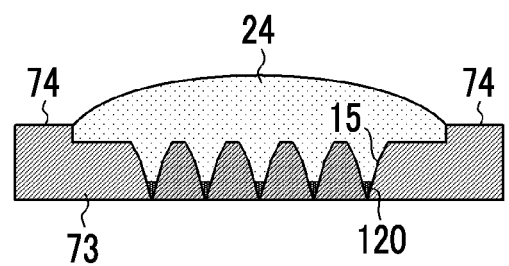
FIG. 29B is an illustration showing the polymer layer forming solution supply step according to the modification example of the first embodiment.

FIGS. 29A and 29B are views showing a modification example of the first embodiment. The mold 73 shown in FIGS. 29A and 29B is different from the mold of the first embodiment in that the step portion 74 is formed in the mold 73 itself. In the case in which the mold 73 has the step portion 74, as described above, the polymer layer forming solution 24 can be fixed to the step portion 74 and a transdermal absorption sheet can be stably produced. The height of the step portion 74 from the region 16 in which the needle-like recessed portions 15 are formed, the coating thickness of the polymer layer forming solution 24, the shape of the periphery of the region in which the needle-like recessed portions are formed which is formed by the step portion as seen from above, or the like can be set as in the above embodiment.

Second Embodiment

Figure 30A:
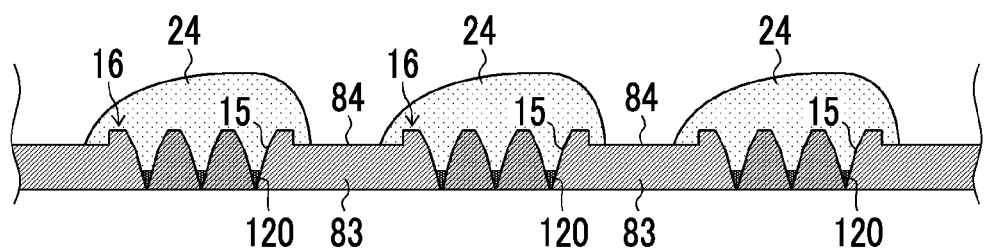
FIG. 30A is an illustration showing a polymer layer forming solution supply step according to a second embodiment.
Figure 30B:
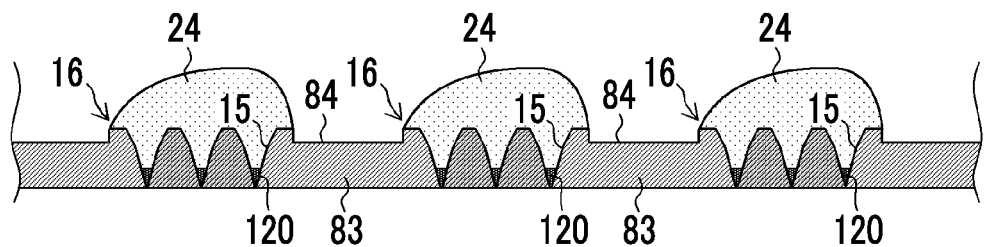
FIG. 30B is an illustration showing the polymer layer forming solution supply step according to the second embodiment.

FIGS. 30A and 30B are illustrations showing a polymer layer forming solution supply step according to a second embodiment of the present invention. The polymer layer forming solution supply step of the second embodiment is different from the polymer layer forming solution supply step of the first embodiment in that the step portion is provided in the periphery of the needle-like recessed portions 15 such that the step portion 84 of the mold 83 having the needle-like recessed portions 15 is set to be lower than the region 16 in which the needle-like recessed portions 15 are formed.

In the second embodiment, as shown in FIG. 30A, the step portion 84 is set to be lower the region 16 of the mold 83 in which the needle-like recessed portions 15 are formed and the polymer layer forming solution 24 is applied in a wide range of equal to or wider than the region 16 in which the needle-like recessed portions 15 are formed, that is, up to the step portion 84. After the polymer layer forming solution 24 is applied, the reduction of the polymer layer forming solution 24 by the surface tension is started and as shown in FIG. 30B, the polymer layer forming solution 24 is fixed to the boundary between the region 16 and the step portion 84 not to cause a further reduction. Thus, a transdermal absorption sheet can be stably formed.

At the time of application of the polymer layer forming solution, the thickness from the region in which the needle-like recessed portions 15 are formed is preferably 5,000 μm or less. By setting the coating thickness of the polymer solution to 5,000 μm or less, the drying rate in the next polymer layer forming solution drying step can be improved.

Figure 31A:
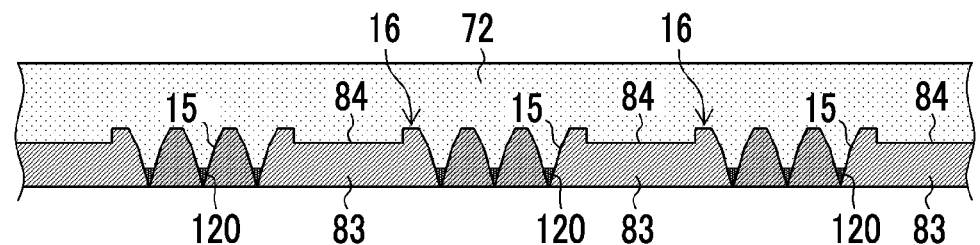
FIG. 31A is an illustration showing an unpreferable example of the polymer layer forming solution supply step.
Figure 31B:
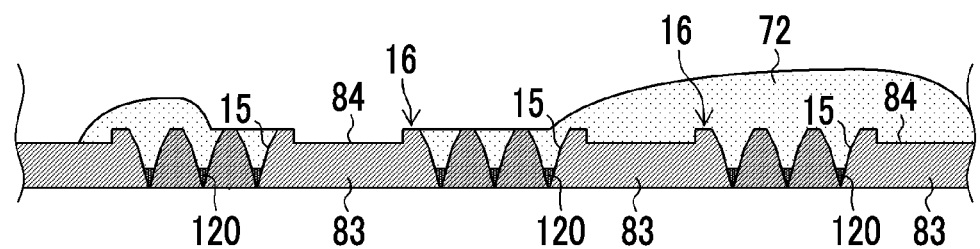
FIG. 31.13 is an illustration showing the unpreferable example of the polymer layer forming solution supply step.

In the second embodiment, the polymer layer forming solution 24 is preferably applied to each region of the needle-like recessed portions 15 surrounded by the step portion 84. FIG. 31A is a view in which the polymer layer forming solution is uniformly applied to the entire surface of the mold 83 having the step portion 84 lower than the region 16 in which the needle-like recessed portions 15 are formed in the periphery of the needle-like recessed portions 15. In the second embodiment, in the case in which the polymer layer forming solution is uniformly applied to the entire surface of the mold 83, the polymer layer forming solution is reduced toward the step portion 84 which is a recessed portion of the mold 83. Accordingly, in the case in which the polymer layer forming solution is uniformly applied to the entire surface of the mold 83, as shown in FIG. 31B, the polymer layer forming solution 24 is repelled from the region 16 in which the needle-like recessed portions 15 are formed and a transdermal absorption sheet may not be stably formed.

In the second embodiment, the shape formed by the step portion in the periphery of the region in which the needle-like recessed portions are formed can be formed into the same shape as in the first embodiment.

(Polymer Layer Forming Solution Drying Step)

Figure 20D:
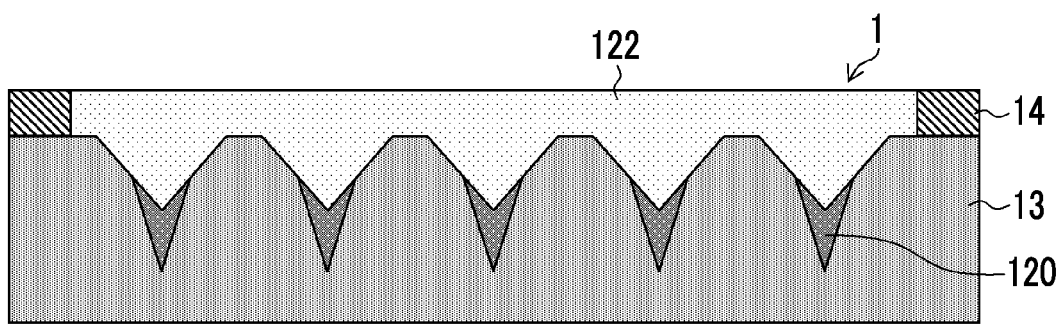
FIG. 20D is schematic view showing a part of the step of producing the transdermal absorption sheet.

Returning to FIG. 20D from FIG. 20A, the polymer layer 122 is formed on the drug layer 120 by drying and solidifying the polymer layer forming solution 24 as shown in FIG. 20D, after the polymer layer forming solution supply step is performed. A polymer sheet 1 having the drug layer 120 and the polymer layer 122 is produced.

In order to stably fix the polymer layer to the frame, quick drying of the polymer layer forming solution at the step portion is effective. The step portion is preferably dried and solidified using dry air, the dry air blowing perpendicular to the mold, at a high temperature and at a low humidity by increasing the wind speed.

In the polymer layer forming solution drying step, the volume of the polymer layer forming solution 24 is reduced by drying. In the case in which the polymer layer forming solution 24 adheres to the mold 13 during drying, a reduction in volume occurs in the film thickness direction of the sheet and thus the film thickness is reduced.

In the case in which the polymer layer forming solution 24 is peeled off from the mold 13 during drying, the polymer sheet 1 shrinks in the plane direction and thus the polymer sheet may be deformed or curled. In the case in which the polymer sheet 1 is peeled off from the mold 13 in a state in which the polymer layer forming solution 24 in the needle-like recessed portion 15 is not sufficiently dried, a defect that the shape of the needle-like protruding portion of the polymer sheet 1 is broken or bent is easily generated. Thus, it is preferable that the polymer sheet 1 is not peeled off from the mold 13 during drying. In addition, in order to suppress curling, a layer which shrinks to the same degree as the surface with the needle-like protruding portion may be formed on the back surface of the polymer sheet 1 (a surface opposite to the surface on which the needle-like protruding portion is formed). For example, a layer is formed so as to have a film thickness at which the effect of suppressing curling has been confirmed in advance by applying the same polymer solution as the surface side to the back surface side.

(Peeling-Off Step)

The method of peeling off the polymer sheet 1 from the mold 13 is not limited. It is desirable that the needle-like protruding portion is not bent or broken during peeling-off. Specifically, a sheet-like base material in which an adhesive layer having adhesive properties is formed is attached to the polymer sheet 1, and then the base material can be peeled off to be turned over from an end portion. In addition, a method in which a sucker is installed on the back surface of the polymer sheet 1 and it is possible to vertically lift the polymer sheet while sucking the polymer sheet by air can be applied. A transdermal absorption sheet 100 is produced by peeling off the polymer sheet 1 from the mold 13.

(Deaeration Step)

The drug solution 22 and/or the polymer layer forming solution 24 is/are preferably subjected to deaeration before the drug solution filling step and/or before the polymer layer forming solution supply step. Through deaeration, the air bubbles contained in the drug solution 22 and the polymer layer forming solution 24 can be removed before the filling of the needle-like recessed portion 15 of the mold 13. For example, in the deaeration step, air bubbles having a diameter of 100 μm to several millimeters are removed.

Examples of the deaeration method include (1) a method of exposing the drug solution 22 under a reduced pressure environment for 1 to 15 minutes, (2) a method of subjecting a container storing the drug solution 22 to ultrasonic vibration for 5 to 10 minutes, (3) a method of applying ultrasonic waves while exposing the drug solution 22 under a reduced pressure environment, and (4) a method of substituting the dissolved gas with helium by sending a helium gas into the drug solution 22. Any of the deaeration methods (1) to (4) also can be applied to the polymer layer forming solution 24.

EXAMPLES

Hereinafter, the present invention will be described in more detail using examples of the present invention. The materials, amounts, ratios, treatment contents, treatment procedures, and the like shown in the following examples can be appropriately changed without departing from the gist of the present invention. Therefore, the scope of the present invention should not be interpreted in a limited manner based on the specific examples illustrated below.

(Production of Mold)

Figure 32A:
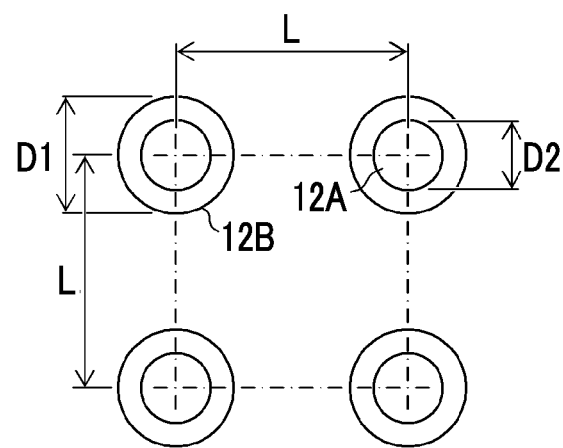
FIG. 32A is a plan view showing an original plate used in Examples.
Figure 32B:
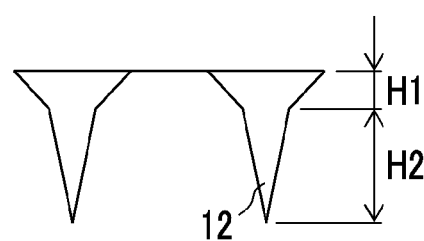
FIG. 32B is a side view showing the original plate used in Examples.

An original plate 11 was produced by subjecting protruding portions 12 each with a needle-like structure to grinding at a pitch L of 1,000 μm in a two-dimensional array with 10 columns and 10 rows on the surface of a smooth Ni plate having one side of 40 mm. As shown in FIGS. 32A and 32B, each protruding portion 12 with a needle-like structure includes a truncated cone 12A with a circular bottom surface having a diameter D1 of 500 μm and a height H1 of 150 μm, and a cone 12B formed on the truncated cone 12A and having a circular bottom surface having a diameter D2 of 300 μm and a height H2 of 500 μm. On the original plate 11, a film with a thickness of 0.6 mm was formed using a silicone rubber (SILASTIC (registered trademark) MDX4-4210, manufactured by Dow Corning Corporation) as a material. The film was thermally cured in a state in which the conical tip end portions of the original plate 11 were projected by 50 μm from the film surface, and then the cured film was peeled off. Accordingly, an inverted article made of silicone rubber having through-holes having a diameter of about 30 μm was produced. The inverted article made of silicone rubber was trimmed so as to leave a planar portion with a side of 30 mm on whose central portion needle-like recessed portions were formed with two-dimensionally arranged in 10 columns and 10 rows and the obtained portion was used as a mold. The surface in which the needle-like recessed portions had wide opening portions served as a surface of the mold, and the surface having through-holes (air vent holes) having a diameter of 30 μm served as a back surface of the mold.

(Preparation of Polymer Solution Containing Drug (Drug Solution))

Hydroxyethyl starch (manufactured by Fresenius Kabi) was dissolved in water to prepare an aqueous solution of 8%. 2% by mass of human serum albumin (manufactured by Wako Pure Chemical Industries, Ltd.) was added to this aqueous solution as a drug to prepare a drug solution. After the solution was prepared, the solution was exposed in an environment of a reduced pressure of 3 kPa for 4 minutes and deaeration was performed.

(Preparation of Polymer Solution (Polymer Layer Forming Solution))

Chondroitin sulfate (manufactured by Manilla Nichiro Corporation) was dissolved in water to prepare an aqueous solution of 40%. The prepared solution was used as a polymer layer forming solution. After the solution was prepared, the solution was exposed in an environment of a reduced pressure of 3 kPa for 4 minutes and sufficient deaeration was performed.

Hereinafter, steps from the drug solution filling step to the polymer layer forming solution drying step were performed in an environment at a temperature of 5° C. and a relative humidity of 35% RH.

(Drug Solution Filling Step and Drug Solution Drying Step)

A drug solution filling apparatus is provided with a driving unit that has a X-axis driving unit and Z-axis driving unit controlling relative position coordinates of the mold and the nozzle decided by an X axis and a Y axis, a liquid supply apparatus (super small amount fixed-quantity dispenser SMP-III, manufactured by Musashi Engineering, Inc.) on which the nozzle can be mounted, a suction base to which the mold is fixed, a laser displacement meter (HL-C201A, manufactured by Panasonic Corporation) that measures the surface shape of the mold, a load cell (LCX-A-500N, manufactured by Kyowa Electronic Instruments Co., Ltd.) that measures a nozzle pressing pressure, and a control system that controls the Z axis based on data of measured values of the surface shape and the pressing pressure.

A gas permeable film (POREFLON (registered trademark) FP-010, manufactured by Sumitomo Electric Industries, Ltd.) having one side of 15 mm was placed on the flat suction base, and the mold was installed thereon such that the surface thereof was positioned on the upper side. The gas permeable film and the mold were fixed to the suction base by pressure reduction with a suction pressure of −90 kPa gauge pressure in the back surface direction of the mold.

A SUS (stainless steel) nozzle having the shape shown in FIG. 14 was prepared, and a slit-shaped opening portion having a length of 12 mm and a width of 2 mm was formed at the center of a lip portion having a length of 20 mm and a width of 0.2 mm. This nozzle was connected to the drug solution tank. The drug solution tank and the nozzle were filled with 3 mL of a drug solution. The nozzle was adjusted such that the opening portion was parallel to the first column of a plurality of needle-like recessed portions formed in the surface of the mold. The nozzle was pressed against the mold at a pressure (pressing force) of 0.14 kgf/cm$^2$ (1.4 N/cm$^2$) at a position apart from the first column with an interval of 2 mm therebetween in a direction opposite to the second column. While being pressed, the nozzle was moved at 1 mm/sec in a direction perpendicular to a length direction of the opening portion while the Z axis was controlled such that the pressing force changed within ±0.05 kgf/cm$^2$ (0.49 N/cm$^2$). Simultaneously, the drug solution was discharged from the opening portion for 10 seconds at 0.31 μL/sec by the liquid supply apparatus. The movement of the nozzle was stopped at a position apart from the tenth column of the plurality of needle-like recessed portions arranged two-dimensionally with an interval of 2 mm therebetween in a direction opposite to the ninth column, and the nozzle was separated from the mold.

The mold filled with the drug solution was put and dried in a windshield (25 cm$^3$) with an opening portion having a diameter of 5 mm. The windshield mentioned herein has a gas permeable film (POREFLON (registered trademark) FP-010, manufactured by Sumitomo Electric Industries, Ltd.) mounted on the opening portion and is structured so as not to be directly exposed to wind.

(Polymer Layer Forming Solution Supply Step and Polymer Layer Forming Solution Drying Step)

On the mold filled with the drug solution, a frame made of stainless steel (SUS304) was placed. Here, while adjusting the discharge amount, the frame, and the clearance of the nozzle, the polymer layer forming solution was directly applied. Then, after 12 hours had passed, whether or not the shape of the transdermal absorption sheet was maintained was confirmed. The evaluation was performed based on the following criteria.

<<Liquid Level Fixation>>

A . . . The polymer layer is fixed to the step portion.

B . . . The polymer layer may not be fixed to the step portion in the case in which this procedure is repeated several times but is in a level not causing a problem.

C . . . The polymer layer is not fixed to the step portion, the polymer layer forming solution is repelled from the mold, and the shape of a transdermal absorption sheet is not stable.

In addition, regarding the sample of which the fixation of the liquid level was evaluated as "A", peeling-off of the sheet was confirmed.

<<Peeling-Off>>

A . . . The sheet is peelable without any problem

B . . . The sheet is not dried and is not peelable after 12 hours has passed when drying starts but is peelable after the drying proceeds and is completed.

C . . . The sheet is not peelable.

Example 1

In the above method, coating was performed by using a circular frame made of SUS at the time of the polymer layer forming solution supply step. The polymer layer forming solution was applied to the frame in a range of 1 mm larger than the size of the frame as a radius. The diameter of the frame is the diameter of the frame, and the height of the liquid level is the coating thickness of the polymer layer forming solution and indicates the height of the step portion formed by installing the frame from the surface of the mold to the liquid level. A test was performed using frames having a diameter of 10, 20, and 30 mm, while setting the same number of needle-like recessed portions and position thereof. Accordingly, a distance from the needle-like recessed portion to the frame can be changed by changing the diameter of the frame. In addition, the height of the liquid level with respect to the height of the frame was changed by changing the height of the frame to 10 to 10,000 μm after the polymer layer forming solution has been applied to evaluate a polymer layer to be formed. The results are shown in Table 1.

TABLE 1

| Test no. | Shape of mold | Shape of step portion | Diameter of frame [mm] | Thickness of frame [μm] | Height of liquid level [μm] | Fixation of liquid level | Peeling-off | EXAMPLE/ COMPARATIVE EXAMPLE |
|---|---|---|---|---|---|---|---|---|
| 1 | None | None | 10, 20, 30 | Not formed | 10 | C | — | COMPARATIVE EXAMPLE |
| 2 | | | | | 100 | C | — | COMPARATIVE EXAMPLE |
| 3 | | | | | 500 | C | — | COMPARATIVE EXAMPLE |
| 4 | | | | | 1,000 | C | — | COMPARATIVE EXAMPLE |
| 5 | | | | | 5,000 | C | — | COMPARATIVE EXAMPLE |
| 6 | | | | | 10,000 | C | — | COMPARATIVE EXAMPLE |

TABLE 1-continued

| Test no. | Shape of mold | Shape of step portion | Diameter of frame [mm] | Thickness of frame [μm] | Height of liquid level [μm] | Fixation of liquid level | Peeling-off | EXAMPLE/ COMPARATIVE EXAMPLE |
|---|---|---|---|---|---|---|---|---|
| 7 | Recessed shape | Circular shape | 10, 20, 30 | 10 | 10 | A | A | EXAMPLE |
| 8 | | | | | 100 | A | A | EXAMPLE |
| 9 | | | | | 500 | A | A | EXAMPLE |
| 10 | | | | | 1,000 | A | A | EXAMPLE |
| 11 | | | | | 5,000 | A | A | EXAMPLE |
| 12 | | | | | 10,000 | A | B | EXAMPLE |
| 13 | Recessed shape | Circular shape | 10, 20, 30 | 10 | 10 | C | — | COMPARATIVE EXAMPLE |
| 14 | | | | | 100 | A | A | EXAMPLE |
| 15 | | | | | 500 | A | A | EXAMPLE |
| 16 | | | | | 1,000 | A | A | EXAMPLE |
| 17 | | | | | 5,000 | A | A | EXAMPLE |
| 18 | | | | | 10,000 | A | B | EXAMPLE |
| 19 | Recessed shape | Circular shape | 10, 20, 30 | 500 | 10 | C | — | COMPARATIVE EXAMPLE |
| 20 | | | | | 100 | C | — | COMPARATIVE EXAMPLE |
| 21 | | | | | 500 | A | A | EXAMPLE |
| 22 | | | | | 1,000 | A | A | EXAMPLE |
| 23 | | | | | 5,000 | A | A | EXAMPLE |
| 24 | | | | | 10,000 | A | B | EXAMPLE |
| 25 | Recessed shape | Circular shape | 10, 20, 30 | 1,000 | 10 | C | — | COMPARATIVE EXAMPLE |
| 26 | | | | | 100 | C | — | COMPARATIVE EXAMPLE |
| 27 | | | | | 500 | C | — | COMPARATIVE EXAMPLE |
| 28 | | | | | 1,000 | A | A | EXAMPLE |
| 29 | | | | | 5,000 | A | A | EXAMPLE |
| 30 | | | | | 10,000 | A | B | EXAMPLE |
| 31 | Recessed shape | Circular shape | 10, 20, 30 | 5,000 | 10 | C | — | COMPARATIVE EXAMPLE |
| 32 | | | | | 100 | C | — | COMPARATIVE EXAMPLE |
| 33 | | | | | 500 | C | — | COMPARATIVE EXAMPLE |
| 34 | | | | | 1,000 | C | — | COMPARATIVE EXAMPLE |
| 35 | | | | | 5,000 | A | A | EXAMPLE |
| 36 | | | | | 10,000 | A | B | EXAMPLE |
| 37 | Recessed shape | Circular shape | 10, 20, 30 | 10,000 | 10 | C | — | COMPARATIVE EXAMPLE |
| 38 | | | | | 100 | C | — | COMPARATIVE EXAMPLE |
| 39 | | | | | 500 | C | — | COMPARATIVE EXAMPLE |
| 40 | | | | | 1,000 | C | — | COMPARATIVE EXAMPLE |
| 41 | | | | | 5,000 | C | — | COMPARATIVE EXAMPLE |
| 42 | | | | | 10,000 | A | B | EXAMPLE |

In the case in which the height from the mold to the liquid level was equal to or higher than the height of the frame, the liquid level could not be fixed to the step portion. In addition, in the example in which the height of the liquid level was 10,000 μm, the liquid level of the polymer layer forming solution was fixed to the step portion. However, it took some time for drying and the solution was not dried after 12 hours had passed from drying. In the above table, the same results were obtained with the frames having diameters of 10 mm, 20 mm, and 30 mm and thus the results were collectively shown.

Example 2

The polymer layer forming solution was applied by using a mold having a step portion in which the region in which the needle-like recessed portions are formed was formed in a projecting shape and the periphery thereof was formed in a recessed shape compared to Example 1. The results are shown in Table 2.

TABLE 2

| Test No. | Shape of mold | Shape of step portion | Diameter of frame [mm] | Thickness of frame [μm] | Height of liquid level [μm] | Fixation of liquid level | Peeling-off | EXAMPLE/ COMPARATIVE EXAMPLE |
|---|---|---|---|---|---|---|---|---|
| 51 | Protruding shape | Circular shape | 10, 20, 30 | 10 | 10 | A | A | EXAMPLE |
| 52 | | | | | 100 | A | A | EXAMPLE |
| 53 | | | | | 500 | A | A | EXAMPLE |
| 54 | | | | | 1,000 | A | A | EXAMPLE |
| 55 | | | | | 5,000 | A | A | EXAMPLE |
| 56 | | | | | 10,000 | A | B | EXAMPLE |

As shown in Table 2, by setting the height of the liquid level to be equal to or higher than the thickness of the frame, the polymer layer could be fixed to the step portion. In addition, in the case in which the height of the liquid level was 10,000 μm, the polymer layer was fixed to the step portion as in Example 1 but was not dried within 12 hours.

Example 3

The shapes of frames used were a square shape to a regular dodecagonal shape (a distance from the center to each apex was 10 mm) and a circular shape having a diameter of 20 mm, and the height of the liquid level was set to 100 μm. In addition, the step portion as formed such that the region in which the mold needle-like recessed portions were formed was formed into a protruding portion, and molds in which the shapes of the step portions are a square shape to a regular dodecagonal shape (a distance from the center to each apex was 10 mm) and a circular shape having a diameter of 20 mm were used to perform a test. The polymer layer forming solution was applied to these molds and the fixation of the polymer layer to the step portion was confirmed. The results are shown in Table 3.

Example 4

The step portion was formed by using a circular SUS frame having a diameter of 20 mm and a thickness of 100 μm used in Example 1 such that the region having needle-like recessed portions was formed in a recessed shape. The height of the liquid level was set to 200 μm and the amount of protrusion to the step portion (the step portion side was set to the outside and the needle-like recessed portion side was set to the inside based on the position of the step portion) was changed to confirm the liquid level fixation of the polymer layer. The results are shown in Table 4.

TABLE 3

| Test No. | Shape of mold | Shape of step portion | Diameter of frame [mm] | Thickness of frame [μm] | Height of liquid level [μm] | Fixation of liquid level | EXAMPLE/ COMPARATIVE EXAMPLE |
|---|---|---|---|---|---|---|---|
| 61 | Recessed shape | Square shape | 20 | 100 | 200 | B | EXAMPLE |
| 62 | | Regular pentagonal shape | | | | B | EXAMPLE |
| 63 | | Regular hexagonal shape | | | | A | EXAMPLE |
| 64 | | Regular octagonal shape | | | | A | EXAMPLE |
| 65 | | Regular dodecagonal shape | | | | A | EXAMPLE |
| 66 | | Circular shape | | | | A | EXAMPLE |
| 67 | Protruding shape | Square shape | 20 | 100 | 200 | B | EXAMPLE |
| 68 | | Regular pentagonal shape | | | | B | EXAMPLE |
| 69 | | Regular hexagonal shape | | | | A | EXAMPLE |
| 70 | | Regular octagonal shape | | | | A | EXAMPLE |
| 71 | | Regular dodecagonal shape | | | | A | EXAMPLE |
| 72 | | Circular shape | | | | A | EXAMPLE |

TABLE 4

| Test No. | Shape of mold | Shape of step portion | Amount of protrusion | Diameter of frame [mm] | Thickness of frame [μm] | Height of liquid level [μm] | Fixation of liquid level | EXAMPLE/ COMPARATIVE EXAMPLE |
|---|---|---|---|---|---|---|---|---|
| 81 | Recessed shape | Circular shape | Uniform coating | 20 | 100 | 200 | A | EXAMPLE |
| 82 | | | 5 mm outside | | | | A | EXAMPLE |
| 83 | | | 1 mm outside | | | | A | EXAMPLE |
| 84 | | | 0.1 mm outside | | | | A | EXAMPLE |
| 85 | | | Same position | | | | A | EXAMPLE |
| 86 | | | 0.1 mm inside | | | | C | COMPARATIVE EXAMPLE |
| 87 | | | 1 mm inside | | | | C | COMPARATIVE EXAMPLE |
| 88 | | | 5 mm inside | | | | C | COMPARATIVE EXAMPLE |

In the case of using the frame, even in the case of using the mold having a step portion to form the region of the needle-like recessed portions into a protruding portion, the shape of the step portion was a square shape, a regular polygonal shape, or the like, and the angle was relatively small. In this case, there was a sample in which the polymer layer forming solution was repelled from the apex portion of the shape of the step portion and the polymer layer could not be fixed to the step portion.

In the cases of Test Nos. 81 to 85 in which the polymer layer forming solution was applied at a position equal to the step portion or wider than the step portion, the polymer layer could be fixed to the step portion. Regarding Test Nos. 86 to 88 in which the polymer layer forming solution was applied to the inside of the frame, the polymer layer could not be fixed to the step portion and repelled in the region of the mold in which the needle-like recessed portions were formed. Thus, a transdermal absorption sheet having a good shape could not be formed.

EXPLANATION OF REFERENCES

1: polymer sheet
11, 71, 81: original plate
12: protruding portion
13, 73, 83: mold
14, 17: frame
15: needle-like recessed portion
15A: inlet portion
15B: tip end recessed portion
15C: through-hole
16: region
18: mold complex
19: gas permeable sheet
20: base
22: drug solution
24: polymer layer forming solution
30: liquid feed tank
32: pipe
34: nozzle
34A: lip portion
34B: opening portion
34C: inclined surface
36: liquid supply apparatus
48: drug solution filling apparatus
50, 54: axis driving unit
52: suction base
56: stand
58: control system
60: displacement meter
74, 75, 84, 85: step portion
92: coating means
100: transdermal absorption sheet
110: needle-like protruding portion
112: needle portion
112A: needle-like portion
112B: body portion
114: frustum portion
116: sheet portion
120: drug layer
122: polymer layer

What is claimed is:

1. A method of producing a transdermal absorption sheet, comprising:
a drug solution filling step of filling needle-like recessed portions of a mold having the needle-like recessed portions with a drug solution that is a polymer solution containing a drug, the mold having a first region in which the needle-like recessed portions are formed, and a second region in a periphery of the first region, the second region being provided with a step portion having a height that is higher than a height of the first region;
a drug solution drying step of drying the drug solution filling the needle-like recessed portions to form a drug layer containing the drug;
a polymer layer forming solution supply step of supplying a polymer layer forming solution to the mold, the supplied polymer layer forming solution being adjusted to have, over a range of greater than the step portion as seen from above, a height higher than a height of the step portion, and to have a first height in a vicinity of a center of the first region and a second height in a periphery of the center of the first region, the second height being higher than the first height, and then contracting the supplied polymer layer forming solution by surface tension, while a contact position of the supplied polymer layer forming solution and the mold is fixed to the step portion; and
a polymer layer forming solution drying step of drying the polymer layer forming solution that has contracted, to form a polymer layer.

2. The method of producing a transdermal absorption sheet according to claim 1,
wherein the height of the step portion of the mold is 10 μm or more and 5,000 μm or less.

3. The method of producing a transdermal absorption sheet according to claim 1,
wherein in the polymer layer forming solution supply step, a thickness of the polymer layer forming solution is 5,000 μm or less.

4. The method of producing a transdermal absorption sheet according to claim 1,
wherein the step portion is a frame that is installed to be separated from the mold.

5. The method of producing a transdermal absorption sheet according to claim 1,
wherein the step portion has a step in the mold itself.

6. The method of producing a transdermal absorption sheet according to claim 1,
wherein the step portion has a tapered shape widening in a direction from the first region to an upper side in a vertical direction.

7. The method of producing a transdermal absorption sheet according to claim 1,
wherein a shape formed by the step portion in the periphery of the first region is a regular hexagonal or higher polygonal shape or a circular shape.

8. A method of producing a transdermal absorption sheet, comprising:
a drug solution filling step of filling needle-like recessed portions of a mold having the needle-like recessed portions with a drug solution that is a polymer solution containing a drug, the mold having a first region in which the needle-like recessed portions are formed, and a second region in a periphery of the first region, the second region being provided with a step portion, the step portion having a height higher than a height of the first region and having a tapered shape widening in a direction from the first region to an upper side in a vertical direction;
a drug solution drying step of drying the drug solution filling the needle-like recessed portions to form a drug layer containing the drug;
a polymer layer forming solution supply step of supplying a polymer layer forming solution the mold, the supplied polymer layer forming solution being adjusted to have, over a range of greater than the step portion as seen from above, a height higher than a height of the step portion, and then contracting the supplied polymer layer forming solution by surface tension, while a contact position of the supplied polymer layer forming solution and the mold is fixed to the step portion; and
a polymer layer forming solution drying step of drying the polymer layer forming solution that has contracted, to form a polymer layer.

9. The method of producing a transdermal absorption sheet according to claim 8, wherein the height of the step portion of the mold is 10 μm or more and 5,000 μm or less.

10. The method of producing a transdermal absorption sheet according to claim 8, wherein in the polymer layer forming solution supply step, a thickness of the polymer layer forming solution is 5,000 μm or less.

11. The method of producing a transdermal absorption sheet according to claim 8, wherein the step portion is a frame that is installed to be separated from the mold.

12. The method of producing a transdermal absorption sheet according to claim 8, wherein the step portion has a step in the mold itself.

13. The method of producing a transdermal absorption sheet according to claim 8, wherein a shape formed by the step portion in the periphery of the first region is a regular hexagonal or higher polygonal shape or a circular shape.

* * * * *